United States Patent
Ahmadizadeh et al.

(10) Patent No.: US 11,581,064 B2
(45) Date of Patent: Feb. 14, 2023

(54) DEVICE-AGNOSTIC SYSTEM FOR PLANNING AND EXECUTING HIGH-THROUGHPUT GENOMIC MANUFACTURING OPERATIONS

(71) Applicant: Zymergen Inc., Emeryville, CA (US)

(72) Inventors: Kiyan Ahmadizadeh, Emeryville, CA (US); Tessa Alexanian, Oakland, CA (US); Barbara Frewen, Alameda, CA (US); Prasad Ganesan, Oakland, CA (US); Aaron Kimball, San Francisco, CA (US); William J. Mania, Richmond, CA (US); Zachary Palchick, Berkeley, CA (US); Erin Rhode, Oakland, CA (US); Dylan Webster, Berkeley, CA (US)

(73) Assignee: Zymergen Inc., Emeryville, CA (US)

( * ) Notice: Subject to any disclaimer, the term of this patent is extended or adjusted under 35 U.S.C. 154(b) by 382 days.

(21) Appl. No.: 16/758,823

(22) PCT Filed: Oct. 25, 2018

(86) PCT No.: PCT/US2018/057583
§ 371 (c)(1),
(2) Date: Apr. 23, 2020

(87) PCT Pub. No.: WO2019/084315
PCT Pub. Date: May 2, 2019

(65) Prior Publication Data
US 2020/0350036 A1    Nov. 5, 2020

Related U.S. Application Data

(60) Provisional application No. 62/577,615, filed on Oct. 26, 2017.

(51) Int. Cl.
*G06F 16/90* (2019.01)
*G16B 30/20* (2019.01)
(Continued)

(52) U.S. Cl.
CPC ......... *G16B 30/20* (2019.02); *G06F 16/9024* (2019.01); *G16B 20/00* (2019.02); *G16B 50/00* (2019.02)

(58) Field of Classification Search
CPC ...... G16B 30/20; G16B 20/00; G06F 16/9024
See application file for complete search history.

(56) References Cited

U.S. PATENT DOCUMENTS 7,826,975 B2 * 11/2010 Maranas ............ G01N 33/5005
702/19
8,108,152 B2    1/2012 Maranas et al.
(Continued)

FOREIGN PATENT DOCUMENTS

JP    2018527674 A    9/2018

OTHER PUBLICATIONS

ABI 3900 High Throughput DNA Synthesizer, User's Manual, 2001, 144 pages, Applied Biosystems, US (retrieved on Mar. 16, 2018 from URL cited in Written Opinion).
(Continued)

*Primary Examiner* — Eliyah S. Harper
(74) *Attorney, Agent, or Firm* — Almanac IP Advisors LLP

(57) ABSTRACT

High-throughput production of modified microbes is achieved through optimization of directed build graph data structures representing biological workflows. Portions of otherwise unrelated workflows may be combined where they share common biological reaction steps, and processed by a genetic manufacturing facility to take advantage of operational efficiencies. Workflows may be mapped to physical
(Continued)

laboratory equipment in a manner that optimizes material transfers. Different automated platforms running different machines in different languages are coordinated in a device-agnostic and language-agnostic manner.

34 Claims, 13 Drawing Sheets

Specification includes a Sequence Listing.

(51) Int. Cl.
    *G06F 16/901*     (2019.01)
    *G16B 20/00*     (2019.01)
    *G16B 50/00*     (2019.01)

(56) References Cited

U.S. PATENT DOCUMENTS

| | | | |
|---|---|---|---|
| 8,332,160 B1 * | 12/2012 | Platt | G16B 30/10 700/1 |
| 2011/0054654 A1 * | 3/2011 | Phillips | G16B 50/30 700/98 |
| 2017/0159045 A1 * | 6/2017 | Serber | C12N 15/1058 |

OTHER PUBLICATIONS

Alper et al, Construction of lycopene-overproducing *E.coli* strains by combining systematic and combinatorial gene knockout targets, Nature Biotechnology May 2015, vol. 23, No. 5, pp. 612-616.
Alter, et al., Singular value decomposition for genome-wide expression data processing and modeling, PNAS, Aug. 20, 2000, pp. 10101-10106, v.97, No. 18.
Antha: a platform for engineering biology, PLOS Blogs, Feb. 20, 2017, 12 pgs.
Autoprotocol, An open standard for life science experimental design and automation, Sep. 13, 2017, 2 pgs.
Bartley et al., "Synthetic biology open language (SBOL) version 2.0.0," Journal of Integrative Bioinformatics (JIB) (2015); 12(2): 902-991.
Beal et al, 2012, An End-to-End Workflow for Engineering of Biological Networks from High-Level Specifications, ACS SyntheticBiology, pp. 317-331, Supporting Information: Method Detail for "An End-to End Workflow for Engineering of Biological Networks from High-Level Specifications" pp. 1-13.
Bilitchenko et al, Eugene—A Domain Specific Language for Specifying and Constraining Synthetic Biological Parts, Devices, and Systems, Apr. 2011, PLoS ONE vol. 6, Issue 4, 40 pgs.
Buchholz et al, Platform Engineering of Corynebacterium glutamicum with Reduced Pyruvate Dehydrogenase Complex Activity for Improved Production of L-Lysine, L-Valine, and 2-Ketoisovalerate, Applied and Environmental Microbiology, Sep. 2013, vol. 79, No. 18, pp. 5556-5575.
Carter, et al., Prediction of phenotype and gene expression for combinations of mutations, Molecular Systems Biology 3:96, 2007, 9 pages.
Chen et al., "DeviceEditor visual biological CAD canvas." Journal of Biological Engineering (2012); 6:1, pp. 1-12.
Concise Description of the Relevance of Alper et al., filed in U.S. Appl. No. 15/396,230 on Dec. 7, 2017, 2 pgs.
Concise Description of the Relevance of Beal et al. and Platt et al., filed in U.S. Appl. No. 15/140,296 on May 18, 2018, 9 pgs.
Concise Description of the Relevance of Beal et al., filed in U.S. Appl. No. 15/140,296 on May 18, 2018, 7 pgs.
Concise Description of the Relevance of Bilitchenko et al., filed in U.S. Appl. No. 15/140,296 on May 18, 2018, 7 pgs.
Concise Description of the Relevance of Buchholz et al., filed in U.S. Appl. No. 15/396,230 on Dec. 7, 2017, 2 pgs.
Concise Description of the Relevance of Gardner et al., filed in U.S. Appl. No. 15/396,230 on Dec. 7, 2017, 1 pg.
Concise Description of the Relevance of Ikeda et al. and Trikka et al., filed in U.S. Appl. No. 15/396,230 on Dec. 7, 2017, 9 pgs.
Concise Description of the Relevance of Ohnishi et al., filed in U.S. Appl. No. 15/396,230 on Dec. 7, 2017, 1 pg.
Concise Description of the Relevance of Pedersen et al., filed in U.S. Appl. No. 15/140,296 on May 18, 2018, 7 pgs.
Concise Description of the Relevance of Platt et al., filed in U.S. Appl. No. 15/140,296 on May 18, 2018, 3 pgs.
Concise Description of the Relevance of Wang et al., filed in U.S. Appl. No. 15/396,230 on Dec. 7, 2017, 2 pgs.
Concise Description of the Relevance of Wilson et al. and Platt et al., filed in U.S. Appl. No. 15/140,296 on May 18, 2018, 10 pgs.
Concise Description of the Relevance of Wilson et al., filed in U.S. Appl. No. 15/140,296 on May 18, 2018, 6 pgs.
Dagre, GitHub, Apr. 17, 2020, 2 pgs, https://github.com/dagrejs/dagre.
Designing a Million Genomes: Machine Learning, Automation and Biotech, Strata+ Hadoop World, Make Data Work conference, London, UK, May 5, 2015; https://youtu.be/658kvYgrJBE, Published on Oct. 7, 2015, Business-focused talk at Strata UK 2015 by Aaron Kimball, CTO of Zymergen Inc.
Final Office Action dated Sep. 20, 2019 in U.S. Appl. No. 15/140,296, 15 pgs.
Frewen et al., "A Detailed, flexible model for sharing DNA concepts." IWBDA 2015, 7th International Workshop on Bio-Design Automation, University of Washington, pp. 66-67, Aug. 19-21, 2015 (Presentation and Poster), 86 pages.
Gardner et al, Production of Citric Acid by Mutants of *Aspergillus niger*, 1956, J. gen. Microbiol. 14, pp. 228-237.
Giaever, et al., Functional profiling of the *Saccharomyces cerevisiae* genome, Nature, Jul. 25, 2002, pp. 387-391, v. 418, Nature Publishing Group.
Hillson, "J5 DNA Assembly Design Automation Software." ACS Synthetic Biology (2011 ); 1: 14-21.
Ikeda et al, A genome-based approach to create a minimally mutated Corynebacterium glutamicum strain for efficient L-lysine production, Society for Industrial Microbiology 2006, 6 pages.
International Search Report for PCT/US2017/029725 dated Sep. 8, 2017, 4 pages.
International Search Report for PCT/US2018/057583 dated Apr. 17, 2019, 7 pgs.
J5 DeviceEditor manual excerpt from hllps://j5.jbei.org/index.php/Main_Page_downloadedcontent available Apr. 19, 2016, 45 pages.
JgraphT, a free Java Graph Library, Oct. 15, 2017, 4 pgs.
Jung, Java Universal Network/Graph Framework, Oct. 25, 2017, 2 pgs.
Kimball, A., "The Data-Driven Future of Biotechnology." Zymergen, Machine learning, automation, and biotech, Strata+ Hadoop World, Make Data Work conference, Presentation, London, UK, May 5, 2015, 49 pages http://cdn.oreillystatic.com/en/assets/1/evenl/132/The%20datadriven%JOfuture%20of'"o20biotechnology%20Presentation.pdf".
Lee et al, A Highly Characterized Yeast Toolkit for Modular, Multipart Assembly, ACS SyntheticBiology 2015, pp. 975-986.
Lee et al, Systems biotechnology for strain improvement, TRENTS in biotechnology, vol. 23 No. 7, Jul. 2005, 10 pages.
Lewis et al., Constraining the metabolic genotype-phenotype relationship using a phylogeny of in silico methods, Nature Reviews, Microbiology, Apr. 2012, pp. 291-305, v. 10, MacMillan Publishers Limited.
LIMS-BPMS Coupling: A Novel Approach for Flexible End-to-End Workflow Automation in Life Science Laboratories, Part 1 Posted: Mar. 11, 2014, 5 pgs.
Neo4j, the world's leading graph database, Oct. 18, 2017, 8 pgs.
Networkx, Software for complex networks, Oct. 24, 2017, 1 pg.
Non-Final Office Action dated Mar. 8, 2019 in U.S. Appl. No. 15/140,296, 20 pgs.
Notice of Allowance dated Sep. 21, 2020 in U.S. Appl. No. 15/140,296, 10 pgs.
Ohnishi et al, A novel methodology employing Corynebacterium glutamicum genome information to generate a new L-lysine-producing mutant, Appl Microbiol Biotechnol (2002) 58: 7 pages.

(56) References Cited

OTHER PUBLICATIONS

PCT Third Party Observation submitted Apr. 6, 2018 for international Patent Application No. PCT/US2016/065465, 12 pages.
PCT Third Party Observation submitted Aug. 24, 2018 for International Patent Application No. PCT/US2017/029725, 5 pgs.
Pedersen et al., "Towards programming languages for genetic engineering of living cells," J.R. Soc. Interface (Apr. 15, 2009), The Royal Society, 6: S437-S450.
Scudellari, Software Startups Aim to Automate Bio Labs, IEEE Spectrum, Apr. 27, 2017, 3 pgs.
Snitkin et al, Epistatic Interaction Maps Relative to Multiple Metabolic Phenotypes, PLoS Genetics, Feb. 2011, vol. 7, Issue 2, 15 pages.
Szappanos, et al., "An integrated approach to characterize genetic interaction networks in yeast metabolism", Nature Genetics (May 29, 2011); 43(7): 656-662.
The Data-Driven future of biotechnology, https://www.youtube.com/watch?v=IYmgJUHcG9g&feature=youtu.be&t=915, Strata+ Hadoop World, NY, Sep. 28-Oct. 1, 2015, Published on Nov 15, 2015, Technical talk at Strata NY 2015 by Aaron Kimball, CTO of Zymergen Inc. about Zymergen's technology.
Third Party Submission filed in U.S. Appl. No. 15/140,296 on May 1, 2018, 3 pgs.
Third Party Submission submitted Dec. 7, 2017 for U.S. Appl. No. 15/396,230, 14 pages.
Third Party Pre-Issuance Submission Transmittal, filed in U.S. Appl. No. 15/140,296 on May 18, 2018, 2 pgs.
Third Party Pre-Issuance Submission Transmittal, filed in U.S. Appl. No. 15/396,230 on Dec. 7, 2017, 2 pgs.
Third Party Submission Under 37 CFR 1.290 Concise Description of Relevance, filed in U.S. Appl. No. 15/140,296 on May 18, 2018, 5 pgs.
Third Party Submission Under 37 CFR 1.290 Concise Description of Relevance, filed in U.S. Appl. No. 15/396,230 on Dec. 7, 2017, 8 pgs.
Transcriptic, Discovery Biology on Demand, The Robotic Cloud Laboratory, Sep. 27, 2017, 9 pgs.
Trikka et al, Iterative carotenogenic screens identify combination of yeast gene deletions that enhance sclareol BioMed Central, Microbial Cell Factories 2015, 14:60, 19 pages.
Wang et al, Programming cells by multiplex genome engineering and accelerated evolution, Nature vol. 460, Aug. 13, 2009, 6 pages.
Wilson et al, Genotype Specification Language, ACS Synthetic Biology 2016, 471-478.
Written Opinion for PCT/US2017/029725 dated Sep. 8, 2017, 6 pages.
Written Opinion for PCT/US2018/057583 dated Apr. 17, 2019, 14 pgs.
Notice of Reasons for Rejection (Translation) dated Oct. 25, 2022 in JP patent application No. 2020-523321, 3 pages.

\* cited by examiner

DEVICE-AGNOSTIC SYSTEM FOR PLANNING AND EXECUTING HIGH-THROUGHPUT GENOMIC MANUFACTURING OPERATIONS

CROSS-REFERENCE TO RELATED APPLICATIONS

This application is a national stage entry of International Application No. PCT/US2018/057583, filed Oct. 25, 2018, which claims the benefit of priority to U.S. provisional application No. 62/577,615, filed Oct. 26, 2017, and is related to International Application No. PCT/US2017/029725 (U.S. Patent Pub. No. US 2017/0316353), filed on Apr. 26, 2017 (the "Codon" application), which claims the benefit of priority to U.S. nonprovisional application Ser. No. 15/140,296, filed on Apr. 27, 2016, all of which are hereby incorporated by reference in their entirety.

STATEMENT REGARDING SEQUENCE LISTING

The Sequence Listing associated with this application is provided in text form in lieu of a paper copy, and is hereby incorporated by reference into the specification. The name of the text file containing the Sequence Listing is 2016-07-28_Sequence_Listing_U.S._15140296.txt. The text file is approximately 4 KB, was created on Jul. 28, 2016, and is being submitted electronically via EFS-Web.

BACKGROUND

Field

The present disclosure is generally directed to high-throughput microbial genomic engineering, and, more particularly, to generating and processing build graph data structures to control production in a gene manufacturing system of a product of interest that incorporates genetic modifications, to generating and processing a data structure for quality control of biological components in a high-throughput system.

Description of Related Art

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also correspond to implementations of the claimed technology.

Microbe engineering enables the generation of novel chemicals, advanced materials, and pharmaceuticals. A strain design company, on behalf of itself or third parties, may modify a previously described DNA segment to enhance the metabolic production of a microbial host by improving output properties such as yield, productivity, optimal growth temperature, growth rate, or titer.

High-throughput production of modified microbes requires high-throughput strain design. Robots are capable of building hundreds to thousands of strains at once, and design tools must be able to match this capacity. Large experiments may explore many different combinations of genetic modifications applied to different parts of a genome.

Prior systems provide as an input to a gene manufacturing process information identifying a nucleotide sequence to be manufactured. From that information, the assembler of the genome is left to determine the best nucleotide parts and workflow to manufacture the sequence. In large-scale operations, many thousands of sequences may be generated by a genomic design program like Eugene. For example, the program may generate 10,000 modified genomes, which would occupy on the order of 50-100 GB of storage space. This information would not fit in a typical memory at this time, and would instead require, for example, slower disk-based access. Embodiments may employ, e.g., SBOL to represent the output DNA components. Current commercial computer systems cannot load and operate efficiently on a 50-100 GB SBOL file. Such operations may crash or cause unacceptable delays in processing.

International Application No. PCT/US2017/029725 (the "Codon application"), assigned to the assignee of the present invention, describes embodiments that overcome the challenges rooted in computer technology when implementing large-scale sequence designs in computer systems. That application provides processes, systems, and data structures for simultaneously introducing multiple mutations in multiple parent nucleotide sequences to transform them into a large set of mutated sequences. Moreover, processing a large number of such output sequences can lead to unacceptably slow processing times or even processing failure. Embodiments described in the Codon application improve industrial-scale genomic design and manufacture by, e.g., reducing time and complexity for the design and building of nucleotide sequences.

Constructing genetically modified organisms at high-throughput requires the execution of biological workflows that employ software and robotics. Automation (robotics) can be used to perform the physical labor of genetic engineering, whereas software can be used to plan the fine-grained details of and record data gathered during the execution of the physical work.

To enhance productivity, some systems model biological processes as workflows (including American Laboratory's LIMS-BPM coupling); however, these software systems do not then make a connection to specific automated platforms that perform the individual steps of the protocols.

On the automation side, the language used to describe a biological protocol or workflow by a scientist does not directly translate into machine instructions for automated platforms that perform the specific steps of the protocol. Furthermore, multiple machines may be used to execute a single protocol, each of which uses a slightly different machine language.

Conventional approaches attempt to partially address these issues. Autoprotocol is a language developed by Transcriptic intended to be used as a common framework for translating higher level protocol descriptions to specific machine instructions. However, Autoprotocol does not define a method for transmitting the instructions across a distributed system of multiple types of platforms. Similarly, Antha is a high level programming language for biological processes that attempts to address similar issues as Autoprotocol and, additionally, is device agnostic. However, it is unclear how easily extensible it is to new platforms and it does not appear to be language agnostic.

Quality Control in high-throughput strain design systems

The Codon application describes a laboratory information management system (LIMS) for the design, building, testing, and analysis of DNA sequences. During testing, microbe strains may be subjected to quality testing (e.g., quality control (QC) assessments) based upon, e.g., size and sequencing methods. The resulting strains that pass QC may then be further processed in furtherance of producing a product of interest, e.g., transferred from liquid or colony cultures on to plates.

The high-throughput strain design system such as that described in the Codon application gives rise to the challenge of performing in silico quality control at all or almost all steps of the workflow along the way to producing the product of interest. Such a high-throughput strain design system can produce many (e.g., 100s or 1000s of) in silico intermediate products. Moreover, the in silico processing of one intermediate product can spawn multiple intermediate products, leading to exponential growth in the number of in silico QC procedures. Thus, performing in silico QC on each intermediate product in such a high-throughput strain design system presents computational challenges during the QC test design phase that would be especially daunting if performed by a human. Moreover, performing QC testing on each intermediate product in a physical, real-world high-throughput gene manufacturing system presents challenges in efficiently assigning reactants and equipment for the QC testing.

SUMMARY

Embodiments of the disclosure provide a software system which models biological workflows of manufacturing activities in a directed build graph that may be created at manufacturing time. Graphs are a known data structure, and general mechanisms exist for storing and querying graphs. However, the inventors do not know of any conventional graph representations of workflows of genetic modifications of biological components. Embodiments of the disclosure use existing libraries. Others were evaluated, including: NetworkX, JUNG, JgraphT, Neo4J, Dagre. While these are general graph databases, they are not specialized for manufacturing processes, biological workflows, or working with DNA as data.

Biologists use the system of embodiments of the disclosure to specify a high-level biological workflow, including inputs and final products. The system determines the intermediate outputs required and the relationships between those components. The workflows are modular and composable. This enables more complicated workflows to be built up from simpler workflows, and also the combination of portions of otherwise unrelated workflows to take advantage of operational efficiencies.

The system maps each set of inputs and outputs of a workflow to (a) physical laboratory equipment based on the relationships described in the workflow, and (b) descriptions of biological protocols for each step in the workflow. The system connects multiple independent software and hardware platforms to manage and execute these activities.

Embodiments of the disclosure improve the execution of high-throughput workflows by taking common aspects of similar biological workflows out of their specific context and performing them together. Embodiments of the disclosure allow common processing of steps for many different workflows where the workflows share the same steps.

On the software side, the grouping of common stages of disparate manufacturing processes in order to create operational efficiencies is a known practice. However, doing so in the context of high-throughput genetic modifications of biological components is not known to the inventors.

Embodiments of the disclosure model biological workflows as manufacturing processes based on roles and relationships between biological components and build products. This modeling allows embodiments of the disclosure to discern common parts of disparate biological processes and group them together on a factory order scale.

Embodiments of the disclosure also overcome the drawbacks of controlling different automated platforms running different machines in different languages. Such embodiments operate in a distributed fashion to enable communication between a software service that hosts scientists' higher level protocol workflows and the individual automation platforms that perform the various tasks that make up the protocols. In addition, embodiments of the disclosure are device-agnostic (can work with any type of automation platform) and language-agnostic (can work with many different software languages at either end of the communication). This reduces the amount of new software and hardware which must be installed to implement biological protocols.

Generating the Build Graph

Embodiments of the disclosure provide systems, methods and computer-readable media storing executable instructions for generating a build graph data structure to control production in a gene manufacturing system of one or more products of interest incorporating genetic modifications.

According to embodiments of the disclosure, a factory order placement engine (otherwise known as an "order placer") accesses a description (e.g., a sequence specification, such as a DNA specification described in detail below) of a biological workflow, wherein the description includes representations of biological components. According to alternative embodiments of the disclosure, a workflow engine accesses descriptions of one or more biological workflows, wherein each description may be represented by a factory order (produced by, e.g., the order placer) and include representations of biological components.

According to embodiments of the disclosure, the workflow engine assembles a build graph data structure based at least in part upon the workflow description. In the build graph data structure, each biological component is represented by a node that resides at a level of a plurality of levels, and each relationship between two biological components is represented by an edge connecting a source node and a destination node. An edge annotation may represent a role of the component that corresponds to the source node.

One or more source nodes (at a given level of the plurality of levels) and a single destination node (at a child level of the given level) that is connected to the one or more source nodes may constitute a reaction group of one or more reaction groups corresponding to the child level. According to embodiments of the disclosure, a source node at the given level within a reaction group may represent a plurality of biological components, and the destination node within the reaction group at the child level may also represent a plurality of biological components. Each reaction group represents a reaction between the one or more biological components that are themselves represented by the one or more source nodes at the given level to produce a biological component represented by the single destination node of the reaction group at the child level. One or more destination nodes at the child level may act as one or more source nodes in a reaction group of one or more reaction groups at a grandchild level of the given level. According to embodiments of the disclosure, at least one of the one or more source nodes at the given level connects to two or more destination nodes at the child level and has a corresponding relationship with each of the corresponding connected two or more destination nodes at the child level.

One or more destination nodes at a final level of the plurality of levels may represent the one or more products of interest, which incorporate genetic modifications caused by reactions among biological components at different levels. Processing the build graph data structure results in production of the one or more products of interest. Products of interest may comprise nucleotides or microbial strains.

According to embodiments of the disclosure, the workflow engine may determine that two or more workflow phases for different factory orders are common workflow phases that may be processed together based at least in part upon a commonality of reaction steps of the common workflow phases. If so, the workflow engine may generate the build graph data structure based at least in part upon the common workflow phases. According to embodiments of the disclosure, the common workflow phases may belong to the same reaction group.

Embodiments of the disclosure provide a workflow engine for processing factory orders to control production in a gene manufacturing system of one or more products of interest incorporating genetic modifications. According to embodiments of the disclosure, the workflow engine accesses a plurality of factory orders, where each factory order indicates one or more genetic design techniques (e.g., promoter swap) for building one or more products of interest. According to embodiments of the disclosure, each workflow phase comprises one or more reaction steps (e.g., electroporation or conjugation).

According to embodiments of the disclosure, the workflow engine may determine that two or more workflow phases for different factory orders of the plurality of factory orders are common workflow phases that may be processed together based at least in part upon a commonality of reaction steps of the common workflow phases. According to embodiments of the disclosure, the workflow engine generates a build graph data structure based at least in part upon the common workflow phases. According to embodiments of the disclosure, the workflow engine may determine the two or more workflow phases or the reaction steps based at least in part upon information from the different factory orders.

According to embodiments of the disclosure, a destination node, at a given level of the build graph data structure, that represents the processing of the common workflow phases, may serve as a source node, at the given level, that connects to two or more destination nodes at a child level of the given level.

According to embodiments of the disclosure, some of the operations performed by the workflow engine may instead be performed by the order placer, particularly in systems where the order placer possesses information concerning physical attributes of the factory, including types of equipment, plate layouts, and biological components available to the factory.

Processing the Build Graph

Embodiments of the disclosure provide a workflow engine for processing a build graph data structure to control production in a gene manufacturing system of a product of interest that incorporates genetic modifications. According to embodiments of the disclosure, the workflow engine accesses a build graph data structure comprising nodes and edges. According to embodiments of the disclosure, each node represents a biological component and resides at a level of a plurality of levels, and each edge connects a source node and a destination node to represent a build relationship between them.

One or more source nodes, at given level of the plurality of levels, and a single destination node, at a child level of the given level, that is connected to the one or more source nodes, may constitute a reaction group of one or more reaction groups corresponding to the child level. Each reaction group represents a reaction between the one or more biological components represented by the one or more source nodes at the given level to produce a biological component represented by the single destination node of the reaction group at the child level. According to embodiments of the disclosure, the workflow engine traverses the build graph data structure at the plurality of levels to map the biological components corresponding to the nodes at the plurality of levels to physical laboratory equipment for producing the product of interest. According to embodiments of the disclosure, mapping the biological components comprises mapping the biological components corresponding to the nodes at the plurality of levels to reactions between biological components.

According to embodiments of the disclosure, traversing the build graph data structure comprises determining one or more layouts of biological components on physical media of one or more respective physical carriers. The layout of biological components represented by nodes on the physical media of the physical carrier may comprise a plate mask.

Determining one or more layouts of biological components on physical media may be based at least in part upon one or more process variations. The one or more process variations may relate to location of physical media on a physical carrier. Determining one or more layouts of biological components on physical media may be based at least in part upon optimizing one or more layouts for efficient transfer of biological components from source physical media to destination physical media. The transfer may be a stamp liquid transfer operation.

According to embodiments of the disclosure, the workflow engine receives a final layout of biological components on physical media of a final physical carrier, where each biological component of the final layout is represented by a destination node at a final level of the build graph data structure, and the workflow engine determines one or more layouts of biological components on physical media of one or more respective physical carriers at corresponding one or more non-final levels of the plurality of levels.

According to embodiments of the disclosure, the workflow engine determines the number of source physical media for sourcing transfer of a corresponding biological component to produce the destination component within each reaction group at the child level based at least in part upon the amount of biological component within the source physical media.

According to embodiments of the disclosure, the workflow engine determines, from the one or more source nodes and the edges within each reaction group of one or more reaction groups at a given level of the build graph data structure, the number of instances of each biological component that corresponds to the one or more source nodes for all reaction groups at the given level that is used to produce one or more destination components corresponding to one or more destination nodes within the one or more reaction groups at the given level.

The workflow engine may then determine the number of source physical media for sourcing transfer of a corresponding biological component to produce the destination component within each reaction group at the given level based at least in part upon the number of instances of the corresponding biological component. The determined number of source physical media for sourcing transfer of a corresponding biological component may be based at least in part upon at least one physical constraint of the source physical media, such as the amount of biological component within the source physical media.

According to embodiments of the disclosure, a physical carrier is a plate and physical media of the physical carrier comprises multiple wells on the plate. According to embodiments of the disclosure, physical media of a physical carrier at a final level of the plurality of levels supports the product of interest. The product of interest may comprise a nucleotide sequence or a microbial strain.

Executing Biological Protocols

Embodiments of the disclosure provide systems, methods and computer-readable media storing executable instructions for implement a factory equipment service interface ("FESI") for implementation of biological protocols on a plurality of automated equipment to generate a product of interest that incorporates genetic modifications. Different pieces of the automated equipment may implement biological protocols pursuant to machine-specific instructions in respective, different machine-specific languages.

According to embodiments of the disclosure, a workflow engine issues object instructions based at least in part upon one or more factory orders, where the object instructions instruct the automated equipment to execute biological protocols. According to embodiments of the disclosure, the workflow engine generates a build graph data structure representing common workflow phases for different factory orders.

Factory worker engines each translate object instructions into machine-specific instructions in a machine-specific language of a plurality of machine-specific languages. Each piece of automated equipment is operable to execute machine-specific instructions in a respective machine-specific language to implement a biological protocol to generate a biological component along a pathway to generating the product of interest. The protocol may, for example, comprise transferring biological components from source physical carriers to destination physical carriers. At least two pieces of automated equipment operate pursuant to different machine-specific languages.

According to embodiments of the disclosure, a protocol broker determines one or more automated equipment that are available to run the biological protocol based at least in part upon messages related to the one or more automated equipment. The protocol may direct object instructions from the workflow engine to corresponding factory workers for the available automated equipment.

Quality Control in High-Throughput Strain Design Systems

QC Test Design

Embodiments of the disclosure provide systems, methods and non-transitory computer readable media for designing quality control testing on a plurality of biological components. Embodiments provide (1) performing, in silico, one or more assays on one or more target biological components, where the in silico performance of each assay on one of the one or more biological components produces one or more assay reaction products (e.g., multiple plasmid fragments) resulting from an assay reaction (e.g., digestion) involving the one of the one or more target biological components (e.g., a plasmid), (2) classifying two or more expected outcomes of each assay as being from the group of: at least one success mode or at least one failure mode, based at least in part upon empirical information concerning the assay; and (3) storing, in an assay data structure, for the one or more assay reaction products, reference information including: (a) attributes of the one or more assay reaction products, and (b) the classification of the two or more expected outcomes.

According to embodiments of the disclosure, processing of the assay data structure results in: (a) performing one or more physical assays, corresponding to the one or more in silico assays, on the one or more target biological components using physical laboratory equipment to generate one or more physical assay reaction products for each physical assay, and (b) for each physical assay, comparing the one or more physical assay reaction products to corresponding reference information to classify the target biological component as corresponding to the at least one success mode or the at least one failure mode.

The target biological components may comprise a plasmid, and the one or more reaction products may comprise plasmid fragments. Each target biological component may comprise a nucleotide sequence or a microbial strain.

The empirical information concerning the assay may comprise empirical information concerning the one or more assay reaction products. Classifying may be based at least in part upon the assay reaction, an assay reactant involved in the assay reaction, and the one of the one or more target biological components. Performing, in silico, one or more assays on one or more target biological components may comprise performing, in silico, at least two assays of the one or more assays on a first target biological component of the one or more target biological components.

The assay data structure can be a directed graph that includes, for the one or more assays on the one or more target biological components, a plurality of levels including a plurality of assay nodes. According to embodiments of the disclosure, in the directed graph, each assay node that resides at a level of a plurality of levels represents one of the one or more of the target biological components, one or more assay reactants, or one or more of the assay reaction products; a target assay node of the plurality of assay nodes represents, at a given level, a target biological component of the one or more target biological components; and an assay reaction product node, of the plurality of assay nodes, that is associated with the target assay node, represents, at a child level of the given level, the one or more assay reaction products and the reference information. According to embodiments of the disclosure, the given level includes at least one assay reactant node representing at least one assay reactant that reacts in silico with the target biological component at the given level. According to embodiments of the disclosure, the target assay node and the assay reactant node at the given level and the assay reaction product node at the child level constitute an assay reaction group of one or more assay reaction groups corresponding to the child level.

Embodiments of the disclosure mitigate challenges of designing QC tests for high throughput strain design systems by taking common aspects of similar QC tests out of their specific context and performing them together. Embodiments of the disclosure allow common processing of steps for many different QC assays where the assays share the same assay reaction steps, similar to the manner in which other embodiments of the disclosure discern common parts of disparate biological processes and group them together on a factory order scale. According to embodiments of the disclosure, each assay comprises one or more assay phases, and each assay phase comprises an assay reaction step of a plurality of assay reaction steps. Embodiments of the disclosure determine that one or more assay phases of different assays are common assay phases that may be processed together based at least in part upon a commonality of the one or more assay reaction steps of the common assay phases, and generate the assay data structure based at least in part upon the common assay phases. The common assay phases may be associated with the same assay reactant. Embodiments of the disclosure determine the quantity of assay reactant needed for the common assay phases. For example, if two common assay phases perform the same assay reaction step on two different biological components, embodiments of the disclosure can compute the total amount of assay reactants needed for the common assay phases, and assign performance of the common assay phases to the appropriate physical laboratory equipment in an efficient manner. During performance of the quality control testing in the physical world embodiments of the disclosure traverse the QC test data structure (e.g., a directed graph of the data structure) to determine the amount of reactant to be used at each piece of physical laboratory equipment for the QC assays.

According to embodiments of the disclosure, classifying comprises classifying the expected outcome of each assay as at least two failure modes based at least in part upon empirical information concerning the assay. According to embodiments of the disclosure, a failure mode represents a defect of the target biological component. According to embodiments of the disclosure, a failure mode represents a failure of the assay. According to embodiments of the disclosure, a first failure mode represents an improperly constructed target biological component according to a first construction error, and a second failure mode represents an improperly constructed target biological component according to a second construction error. According to embodiments of the disclosure, a failure mode represents a defective assay reactant. Embodiments of the disclosure may classify the expected assay outcomes according to any combination of the above success and failure modes.

According to embodiments of the disclosure, for the one or more assay reaction products of an assay reaction, the reference information further comprises identification of: the assay reaction, the one or more assay reaction products, or the assay reactant. The reference information atttributes may include expected length, sequence, or growth capacity of the one or more assay reaction products.

According to embodiments of the disclosure, each of the one or more target biological components is produced in accordance with at least a portion of a build graph data structure, where each node that resides at a level of a plurality of levels of the build graph data structure represents at least one of one or more biological components. According to embodiments of the disclosure, the build graph data structure controls production in a gene manufacturing system of a product of interest, wherein the product of interest incorporates genetic modifications represented by the build graph, According to embodiments of the disclosure, one or more source nodes, at a given level of the plurality of levels of the build graph data structure, and a destination node, at a child level of the given level of the build graph data structure, that is associated with the one or more source nodes, constitute a reaction group of one or more reaction groups corresponding to the child level of the build graph data structure. According to embodiments of the disclosure, each reaction group represents a reaction between one or more biological components that are themselves represented by the one or more source nodes at the given level, to produce one or more of the target biological components represented by the destination node of the reaction group at the child level of the build graph data structure.

QC Test Implementation

Embodiments of the disclosure perform quality control testing on a target biological component, by obtaining information concerning one or more physical assay reaction products resulting from a physical assay of a target biological component; and comparing the one or more physical assay reaction products to corresponding reference information to classify the target biological component as corresponding to at least one success mode, to at least one failure mode, or to an indeterminate mode wherein the reference information includes expected attributes of the one or more physical assay reaction products corresponding to success and failure modes.

If the target biological component is classified as corresponding to the indeterminate mode, embodiments of the disclosure indicate that the physical assay should be performed again. If the target biological component is classified as corresponding to the at least one success mode, embodiments of the disclosure provide instructions for further processing of the target biological component in furtherance of producing a product of interest. A failure mode may represent a defect of the target biological component. A failure mode may represent a failure of the physical assay. According to embodiments of the disclosure, a first failure mode represents an improperly constructed target biological component according to a first construction error, and a second failure mode represents an improperly constructed target biological component according to a second construction error. According to embodiments of the disclosure, a failure mode represents a defective assay reactant used in a physical assay reaction of the physical assay. Embodiments of the disclosure may classify the target biological component according to any combination of the above success, failure and indeterminate modes. Embodiments of the disclosure produce a microbial strain using the quality control testing of any of the applicable embodiments described herein.

Build Graph Extensions

Embodiments of the disclosure provide systems, methods and non-transitory computer readable media for generating a build graph data structure for controlling production in a gene manufacturing system of at least one product of interest incorporating genetic modifications. Embodiments of the disclosure access a description of a biological workflow, wherein the description includes representations of biological components; and assemble a build graph data structure based at least in part upon the workflow description. According to embodiments of the disclosure, in the build graph data structure, each node that resides at a level of a plurality of levels represents one or more of the biological components. According to embodiments of the disclosure, each biological component is a nucleotide, a nucleotide sequence, or a microbial strain. According to embodiments of the disclosure, one or more source nodes, at a given level of the plurality of levels, and a destination node, at a child level of the given level, that is associated with the one or more source nodes, constitute a reaction group of one or more reaction groups corresponding to the child level. According to embodiments of the disclosure, each reaction group represents a reaction between one or more biological components that are themselves represented by the one or more source nodes at the given level, to produce one or more biological components represented by the destination node of the reaction group at the child level. According to embodiments of the disclosure, one or more destination nodes at the child level act as one or more source nodes in one or more reaction groups at a grandchild level of the given level. According to embodiments of the disclosure, at least one destination node at a final level of the plurality of levels represents the at least one product of interest, which incorporates genetic modifications caused by reactions among biological components at one or more different levels. According to embodiments of the disclosure, processing the build graph data structure results in production of the at least one product of interest.

Non-Deterministic Operations on Biological Components

According to embodiments of the disclosure, the destination node in a first reaction group of the one or more reaction groups represents a non-deterministic set of biological components computed to result from one or more reactions applied to one or more biological components represented by the one or more source nodes in the first reaction group. According to embodiments of the disclosure, the destination node represents the non-deterministic set of biological components computed to result from insertion of one of one or more first biological components at one or more non-deterministic locations of a second biological component, wherein the second biological component is a biological sequence. According to embodiments of the disclosure, the destination node represents the non-deterministic set of biological components computed to result from non-deterministic changes to one or more biological components at one or more corresponding, specified locations within a second biological component, wherein the second biological component is a biological sequence. According to embodiments of the disclosure, the non-deterministic changes are limited to a replacement at each of the one or more specified locations within the second biological component with one of the one or more first biological components. According to embodiments of the disclosure, each first biological component is a nucleotide and the second biological component is a nucleotide sequence. According to embodiments of the disclosure, a first biological component of the biological components is a plasmid payload and a second biological component of the biological components is a plasmid backbone.

According to embodiments of the disclosure, the one or more biological components that are represented by the one or more source nodes at the given level of the build graph data structure are microbial strains, and a reaction between the strains comprises horizontal gene transfer between the strains.

Embodiments of the disclosure provide systems, methods and non-transitory media storing instructions for generating a factory order to control production of biological sequences by a gene manufacturing system. Embodiments of the disclosure (1) receive an expression indicating a first non-deterministic operation on a first sequence operand, wherein sequence operands represent biological sequence parts, the first sequence operand representing one or more biological sequence parts; (2) execute instructions to evaluate the expression to a sequence specification, wherein the sequence specification comprises a data structure including (a) one or more first-level non-deterministic operations, including the first non-deterministic operation, to be performed on one or more first-level sequence operands including the first sequence operand, and (b) one or more second-level operations, the execution of which resolves one or more values of the one or more first-level sequence operands; and (3) generating a factory order based upon execution of one or more of the first-level operations and one or more of the second-level operations, the factory order for use by the gene manufacturing system to generate biological sequence parts, wherein the one or more first-level non-deterministic operations correspond to protocols for generating the biological sequence parts.

According to embodiments of the disclosure, the one or more first-level non-deterministic operations also correspond to physical laboratory equipment for generating the biological sequence parts. Embodiments of the disclosure employ a directed build graph data structure to generate the factory order, determine that two or more workflow phases for different factory orders are common workflow phases that may be processed together based at least in part upon a commonality of reaction steps of the common workflow phases, and assemble the build graph data structure based at least in part upon the common workflow phases.

Embodiments of the disclosure produce a microbial strain by any of the preceding methods of the embodiments of the disclosure described above.

These and other embodiments are more fully described below.

DETAILED DESCRIPTION

Figure 1:
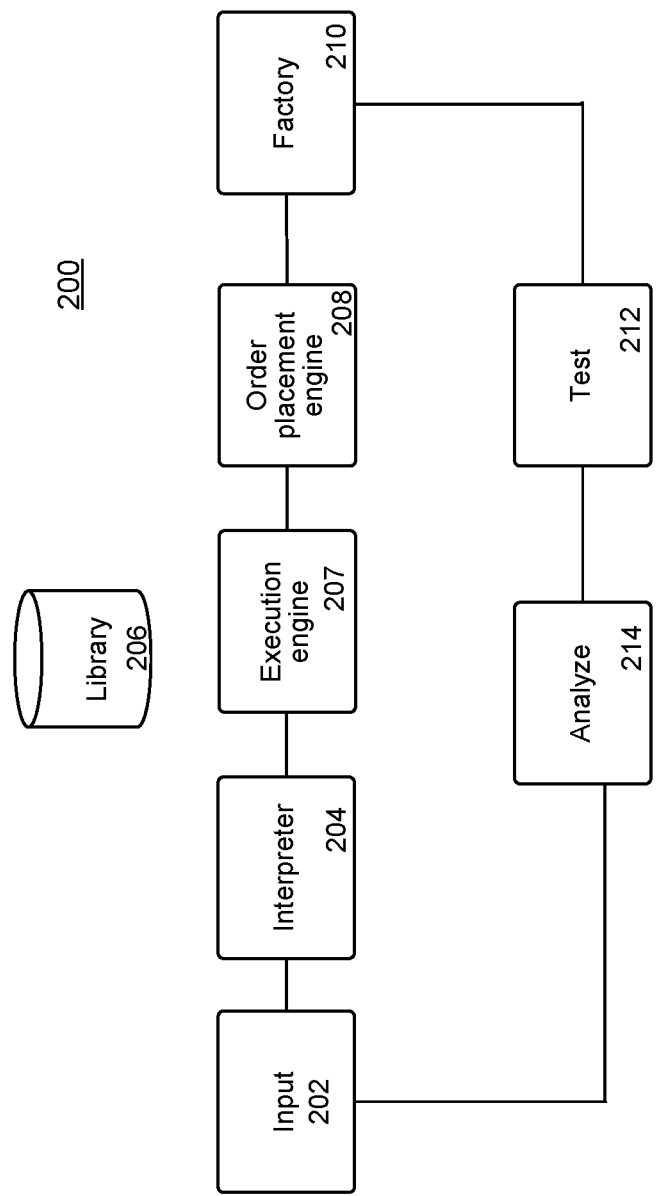
FIG. 1 illustrates a laboratory information management system of embodiments of the disclosure for the design, building, testing, and analysis of nucleotide sequences.

The present description is made with reference to the accompanying drawings, in which various example embodiments are shown. However, many different example embodiments may be used, and thus the description should not be construed as limited to the example embodiments set forth herein. Rather, these example embodiments are provided so that this disclosure will be thorough and complete. Various modifications to the exemplary embodiments will be readily apparent to those skilled in the art, and the generic principles defined herein may be applied to other embodiments and applications without departing from the spirit and scope of the disclosure. Thus, the present disclosure is not intended to be limited to the embodiments shown, but is to be accorded the widest scope consistent with the principles and features disclosed herein.

Embodiments of the Codon application (much of which is directly recited in this disclosure) include the generation of a factory order to control production of nucleotide sequences by a gene manufacturing system. Systems, methods, and computer readable media are described that: receive an expression indicating an operation on sequence operands, each representing at least one nucleotide sequence part; evaluating the expression to a sequence specification, wherein the sequence specification comprises a data structure including one or more first-level operations and one or more second-level operations; and generating a factory order based upon execution of the one or more first-level operations and the one or more second-level operations. In a recursive manner, the one or more first-level operations operate on at least one first-level sequence operand, the value of which is resolved by execution of one or more of the second-level operations. The factory order may then be provided to the gene manufacturing system to assemble the sequence parts into nucleotide sequences represented by the sequence specification.

In embodiments of the disclosure, the factory order may be based on parameters, included in the specification data structure, that relate to how one or more of the first-level operations or one or more second-level operations are to be reified (physically achieved) by the gene manufacturing system. In some embodiments, the parameters may include a first parameter to be used by the gene manufacturing system in the reification of a first second-level operation of the one or more second-level operations, and a second parameter, different from the first parameter and representing the same category of parameters as the first parameter, to be used by the gene manufacturing system in the reification of a second second-level operation of the one or more second-level operations. As examples, the first parameter may indicate a first assembly method, temperature, sequence part source, or primer source, and the second parameter may indicate a second, different assembly method, temperature, sequence part source, or primer source, respectively.

In the process of generating a factory order, the recursive data structure described in the Codon application may be traversed to extract the collection of output strain or DNA designs along with input and intermediate parts that would be used in the construction of these designs. In embodiments of the Codon application, the data structure that holds these input, intermediate, and final DNA sequences is denoted a "factory build graph." This factory build graph (hereafter alternately referred to as a "build graph") may be used along with a predefined workflow for performing the DNA sequence assembly work, to produce the desired output designs in physical form.

System Overview

Figure 2:
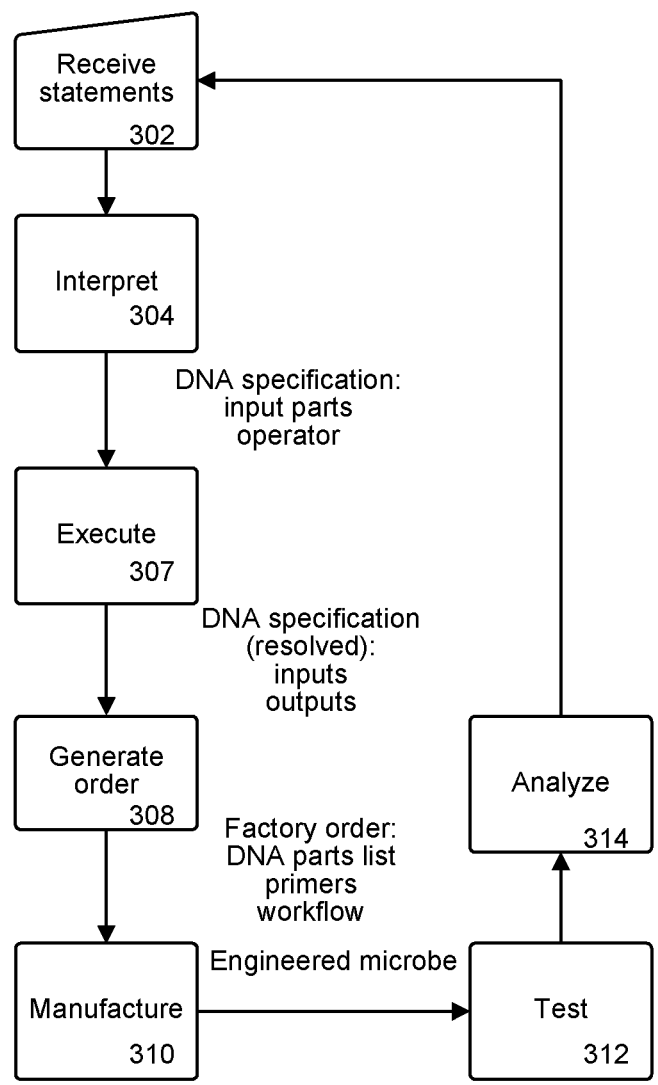
FIG. 2 is a flow chart illustrating a process for designing and building nucleotide sequences, according to embodiments of the disclosure.

FIG. 1 is a system diagram of a laboratory information management system (LIMS) 200 of embodiments of the disclosure for the design, building, testing, and analysis of DNA sequences. FIG. 2 is a corresponding flow diagram. In embodiments of LIMS, one or more changes are made to an input DNA sequence at a time, resulting in a single output sequence for each change or change set. To optimize strains (e.g., manufacture microbes that efficiently produce an organic compound with high yield), LIMS produces many such DNA output sequences at a time, so that they may be analyzed within the same timeframe to determine which host cells, and thus which modifications to the input sequence, best achieve the desired properties. As will be seen below, the genomic design language of embodiments of the disclosure provides compact, human-readable expressions to generate many genome designs in parallel.

In some embodiments the system enables the design of multiple nucleotide sequence constructs (such as DNA constructs like promoters, codons, or genes), each with one or more changes, and creates a work order (i.e., "factory order") to instruct a gene manufacturing system, factory 210, to build the nucleotide sequence constructs in the form of microbes carrying the constructs. According to embodiments of the disclosure, the factory order may be reified by a factory build graph along with a predefined manufacturing execution workflow. Examples of microbes that may be built include, without limitation, hosts such as bacteria, fungi, and yeast. According to the system, the microbes are then tested for their properties (e.g., yield, titer). In feedback-loop fashion, the results are analyzed to iteratively improve upon the designs of prior generations to achieve more optimal microbe performance.

Although the disclosure primarily refers to DNA constructs, those skilled in the art will recognize that the embodiments herein may readily be extended to any nucleotide sequence/nucleic acid sequence (e.g., messenger RNA, any such sequence in an IUPAC alphabet) and is not just limited to DNA sequences. Moreover, although the design, build, test and analysis process is described herein primarily in the context of microbial genome modification, those skilled in the art will recognize that this process may be used for desired gene modification and expression goals in any type of host cell.

Referring to FIGS. 1 and 2 in more detail, an input interface 202, such as a computer running a program editor, receives statements of a program/script that is used to develop the design of one or more DNA output sequences (see 302 in FIG. 2). Such a genomic design program language may be referred to herein as the "Codon" programming language developed by the assignee of the present invention. A powerful feature of embodiments of the disclosure is the ability to develop designs for a very large number of DNA sequences (e.g., microbial strains, plasmids) within the same program with just a few procedural statements.

Program statements may comprise a keyword, specifying an operation, and at least one argument, a function call designated by a function name to call followed by zero or more arguments (whose return value is then discarded upon evaluation), or an assignment of an expression or value to a variable which can be included in subsequent expressions by the variable's name. An expression is a collection of symbols that can be evaluated (resolved) to a value. A function call may be used as a statement or an expression.

Figure 7:
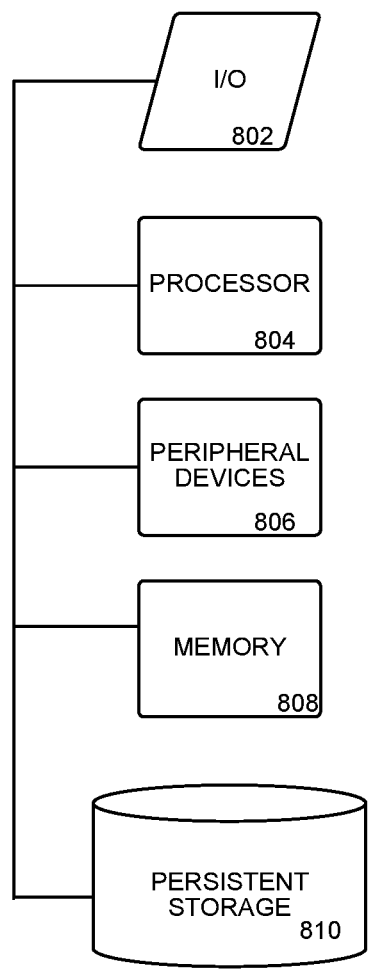
FIG. 7 illustrates an example of a computer system that may be used to implement embodiments of the disclosure.

Here, the editor enables a user to enter and edit the program, e.g., through graphical or text entry or via menus or forms using a keyboard and mouse on a computing device, such as that described with respect to FIG. 7. Those skilled in the art will recognize that other input interfaces 202 may be employed without the need for direct user input, e.g., the input interface 202 may employ an application programming interface (API), and receive statements in files comprising the program from another computing device.

The input interface 202 may communicate with other elements of the system over local or remote connections.

An interpreter or compiler/execution unit 204 evaluates program statements into novel DNA specification data structures of embodiments of the disclosure (304). Data structure details will be described below. (A "DNA specification" may also be referred to herein according to its data type "DnaSpecification." Moreover, the term "DNA specification" is not limited to just DNA sequences, but rather applies to any nucleotide sequence. The "DNA specification" as used herein refers to a specification of how to create one or more DNA/nucleotide sequence(s) from input arguments and an instruction such as "concatenate." If the DNA specification is evaluated, then it may also record its output sequences as described below.)

The terms "interpreter" and "compiler/execution unit" shall be used interchangeably herein, as embodiments of the disclosure may be implemented with either an interpreter or a compiler; the program statements may be either interpreted or compiled. If a compiler is employed, it would be followed by an execution unit in the system of the disclosure.

Typically, at the end, the program script will include a "create" statement identifying the DnaSpecification representing the program's final output to include in a "design campaign." The design campaign itself is a precursor to a factory order for the production of DNA sequences, as will be described below. One or more create statements may be provided; if multiple such statements are used, the collection of DNA specifications is held together in a top-level "list" specification.

The interpreter 204 evaluates the DNA specification argument of the create statement into the design campaign represented via the DnaSpecification data type. The create statement itself may include an indicator (e.g., a flag or other indicator) read by an order placement engine 208 indicating that the argument of the create statement is to be used to generate a factory order for producing a sequence identified by the argument.

In embodiments of the disclosure, at this stage, the interpreter 204 may execute the operations specified by the DNA specification so that its data structure includes resolved outputs. However, in other embodiments, the interpreter 204 would not execute those operations, and the output DNA specification data structure would not include any outputs that have been resolved. Instead, as described below, an execution engine 207 would resolve the outputs.

In evaluating expressions, the interpreter 204 may refer to one or more sources of DNA sequence data, such as custom/local databases, public databases, or user-provided files (collectively referred to herein as a "library" for the sake of convenience). Similar to the design of electronic circuits, synthetic biology designs may be composed hierarchically from libraries of reusable components. A library 206 may include data (e.g., annotations) reflecting properties of DNA sequences and microbes. For example, the library may include data representing the DNA sequences for different strains of *E. coli*, the locations of promoters and terminators within known DNA sequences, and the locations of genes within a microbial strain. The library may, for example, include a database containing thousands of DNA components—some of them entire microbial strain genomes, some of them smaller gene parts. Codon statements may refer to any of these by a unique ID. The library 206 may also refer to the outputs of prior Codon evaluation runs—design campaigns or factory orders—both of which may be embodied in the DnaSpecification data type. In particular, the library 206 may store "libraries" of genotype-phenotype correlation data resulting from the analysis phase describe herein, to allow for the selection of base strains and genetic modifications as candidates to achieve desired phenotypic properties for new factory runs.

DnaSpecifications may also be referred to by ID. According to embodiments of the disclosure, IDs may be issued by the interpreter 204 in non-overlapping sequences to DnaComponents and DnaSpecifications alike, so they may be used interchangeably as inputs within a library. However, by using separate lookup functions for DnaComponents and DnaSpecifications, the system and the user can differentiate between DnaComponents and DnaSpecifications even if the same ID would be a valid identifier for either a DnaComponent or DnaSpecification within the collection of each type. In addition, the library may store a DNA sequence in a file (typically in FASTA or genbank format) that can be used in the Codon script.

In embodiments, an execution engine 207, instead of the interpreter 204, may execute the DNA specification (307). For example, the execution engine 207 may execute one or more operators specified by the DNA specification, applying the operators to the appropriate inputs specified by the DNA specification. At this point, the DNA specification data structure would include the resulting resolved outputs, as well as the one or more operators and inputs (and parameters, discussed below). These outputs may be expressed as an ordered list of DNA components (e.g., cross-product elements described in examples below).

In embodiments, the order placement engine (alternatively called a specification/campaign interpreter or factory order placer) 208 interprets the DNA specification representing the design campaign and determines which intermediate DNA parts will be produced or will be needed as inputs to the factory 210 (308). In general, in some embodiments, the factory order placer 208 requires two inputs: a DnaSpecification and workflow information to indicate what is being built (DnaSpec) and how the user intends to build it (workflow). Based on that, the factory order placer 208 can compute the intermediate parts that will be required for that workflow process using libraries of known parameters and known algorithms that obey known heuristics and other properties (e.g., optimal melting temperature to run on common equipment). In embodiments of the disclosure, the sequence specification itself may specify intermediate inputs as well as parameters indicating workflows and properties for beginning, intermediate and final operations.

Through the factory build graph, the order placement engine 208 transforms the DNA specification from a logical specification into a physical manufacturing process. The precursor and intermediate parts required for the workflow process, as identified by the order placement engine 208 in the manner described above, along with the outputs identified in the executed DnaSpecification, are recorded by the order placement engine 208 into the factory build graph data structure. (The precursor nucleotide sequence parts, e.g., primers, are the starting parts of the nucleotide sequence assembly process—those parts other than intermediate parts/assemblies or final parts/strains—and have no dependencies upon other sequences in the build graph.) In embodiments, this is a directed acyclic graph (DAG) where: each node represents a nucleotide sequence part such as a precursor sequence part, an intermediate sequence part, or a final sequence part, or a final strain; and edges are used to communicate which biological components are inputs to a process creating a particular further intermediate or output part. The particular "role" of each precursor or intermediate part in producing its successor(s) is also recorded in each edge of the build graph (i.e., in the portion of the data structure representing the edge) by the order placement engine 208. The particular shape of the build graph is defined by the user-provided workflow, which is a representation of the actual physical steps performed in a particular laboratory protocol that would produce, through a series of changes, the final desired design. The order placement engine 208 may determine each role from a priori knowledge of the role necessitated by the workflow.

The resulting factory order may include a combination of a prescribed set of steps, as well as the parameters, inputs and outputs for each of those steps for each DNA sequence to be constructed. The factory order may include a DNA parts list including a starting microbial base strain, a list of primers, guide RNA sequences, or other template components or reagent specifications necessary to effect the workflow, along with one or more manufacturing workflow specifications for different operations within the DNA specification, as discussed further below. These primary, intermediate, and final parts or strains may be reified via a factory build graph; the workflow steps refer to elements of the build graph with various roles. The order placement engine 208 may refer to the library 206 for the information discussed above. This information is used to reify the design campaign operations in physical (as opposed to in silico) form at the factory 210 based upon conventional techniques for nucleotide sequence synthesis, as well as custom techniques developed by users or others.

For example, assume a recursive DNA specification has a top-level function of circularize and its input is a chain of concatenate specifications. The factory order placer 208 may interpret that series of inputs such that a person or robot in the lab may perform a PCR reaction to amplify each of the inputs and then assemble them into a circular plasmid, according to conventional techniques or custom/improved techniques developed by the user. The factory order may specify the PCR products that should be created in order to do the assembly. The factory order may also provide the primers that should be purchased in order to perform the PCR.

In another example, assume a DNA specification specifies a top-level function of replace. The factory order placer 208 may interpret this as a cell transformation (a process that replaces one section of a genome with another in a live cell). Furthermore, the inputs to the replace function may include parameters that indicate the source of the DNA (e.g. cut out of another plasmid, amplified off some other strain).

The order placement engine 208 may communicate the factory order to the factory 210 over local or remote connections. Based upon the factory order, the factory 210 may acquire short DNA parts from outside vendors and internal storage, and employ techniques known in the art, such as the Gibson assembly protocol or the Golden Gate Assembly protocol, to assemble DNA sequences corresponding to the input designs (310). As discussed in more detail below with respect to the factory build graph, the roles assigned to edges in the graph specify how the components corresponding to nodes of the build graph are to be used in various techniques (e.g., Gibson assembly) and how they are combined in a multiplexed operation (such as happens on a 96-well plate). The factory order itself may specify which techniques to employ during beginning, intermediate and final stages of manufacture. For example, many laboratory protocols include a PCR amplification step that requires a template sequence and two primer sequences. The factory 210 may be implemented partially or wholly using robotic automation.

According to embodiments of the disclosure, the factory order may specify the production in the factory 210 of hundreds or thousands of DNA constructs, each with a different genetic makeup. The DNA constructs are typically circularized to form plasmids for insertion into the base strain. In the factory 210, the base strain is prepared to receive the assembled plasmid, which is then inserted.

The resulting DNA sequences assembled at the factory 210 are tested using test equipment 212 (312). During testing, the microbe strains are subjected to quality control (QC) assessments based upon size and sequencing methods. The resulting, modified strains that pass QC may then be transferred from liquid or colony cultures on to plates. Under environmental conditions that model production conditions, the strains are grown and then assayed to test performance (e.g., desired product concentration). The same test process may be performed in flasks or tanks.

In feedback-loop fashion, the results may be analyzed by analysis equipment 214 to determine which microbes exhibit desired phenotypic properties (314). During the analysis phase, the modified strain cultures are evaluated to determine their performance, i.e., their expression of desired phenotypic properties, including the ability to be produced at industrial scale. The analysis phase uses, among other things, image data of plates to measure microbial colony growth as an indicator of colony health. The analysis equipement 214 is used to correlate genetic changes with phenotypic performance, and save the resulting genotype-phenotype correlation data in libraries, which may be stored in library 206, to inform future microbial production.

LIMS iterates the design/build/test/analyze cycle based on the correlations developed from previous factory runs. During a subsequent cycle, the analysis equipment 214, alone or in conjunction with human operators, may select the best candidates as base strains for input back into input interface 202, using the correlation data to fine tune genetic modifications to achieve better phenotypic performance with finer granularity. In this manner, the laboratory information management system of embodiments of the disclosure implements a quality improvement feedback loop.

Data Structures

Unlike some conventional techniques for nucleotide sequence assembly, embodiments of the disclosure do not require an input of literal strings directly representing desired sequences. The editor or other input interface may instead, or in addition, receive statements expressed in a high-order genomic description language of embodiments of the disclosure. As indicated above, each high-order statement evaluates to a "DNA specification," having data type DnaSpecification, in embodiments of the disclosure. The DNA specification is a data structure indicating at least one operation on at least one DNA part represented by at least one DNA operand (of data type DnaInput). (A DNA "part" herein refers to a DNA sequence, e.g., a promoter, a gene, a terminator, or any combination thereof. More generally, embodiments of the disclosure apply to any nucleotide sequence parts.) A DnaInput may be either a DnaComponent (an unambiguous representation of a single DNA sequence) or another DnaSpecification. The input itself may be the output of a previous Codon statement within the script or a Codon script output from a prior run/evaluation of the script, giving rise to a recursive data structure describing an ordered set of operations to perform on other DnaInputs specified as arguments to that DnaSpecification.

In some embodiments, a DNA specification may indicate a unary operation to be performed on a DNA part (e.g., circularize), or a binary operation to be performed on two or more DNA parts (e.g., concatenate, replace). In some embodiments, the DNA specification describes combinatorial assemblies of DNA sequences.

In short, a DNA specification may provide:
a structured collection of DNA components
a compact representation of DNA sequence relationships
a concise description of combinatorial design
a nested organization for varying layers of detail and abstraction
an exchange format between designers and manufacturers of DNA assemblies A DNA specification, in some embodiments, has three parts:
One or more sets of ordered inputs
one or more modifying actions
one set of ordered outputs Note that even in the case of functions taking "unary" inputs, such as the circularize function, the "unary" input may itself be a list of inputs. In this case, execution of the function would emit a list of circularized DNA sequences, each created from a single linear input sequence from the list. Binary functions (e.g., concatenate) may operate on two such lists, combining elements of each list as specified by a function modifier (DOT (dot product) or CROSS (cross product)) that indicates whether the elements of the two lists are combined via a "zipper" (dot product) operation (for input lists L and R, for all T, L[i] OP R[i], where "OP" represents a dot product operation), or via a "cross product" operation (for input lists L and R, for all 'i', for all 'j', L[i] OP R[j], where "OP" here represents a cross product operation). The result for each list may respectively be viewed as a vector or a matrix.

In some embodiments, a DNA operand within a DNA specification may be represented as either a DNA specification itself or as a DNA component, and a DNA component may represent a DNA part with a literal alphanumeric string directly representing a sequence of nucleotides. In some embodiments, as mentioned above the DNA component may also include metadata annotations describing properties of a DNA part, such as identification number, source, molecular form (e.g., linear, circular).

Notably, as described above, in some embodiments the DNA operand of the DNA specification may represent a list of DNA parts. These lists of parts can be a list of DNA components, a DNA specification, or a list of DNA specifications.

DNA Component

As a prelude to a discussion of DNA specifications, an example of a DNA component, using the dna( ) function, follows:
sequence="GATACA"
print "The sequence is:"+sequence
myFirstDna=dna(sequence)
print "Here is a DnaComponent:"
print myFirstDna In this example, the interpreter would return:
The sequence is: GATACA
Here is a DnaComponent:
DnaComponent:
  Id: −1
  Name: dna string
  Description: literal: GATACA
  Molecular form: LINEAR
  Sequence: GATACA Using DNA components, the interpreter 204 enables specifying a DNA sequence directly in the script, or by loading it from the library. For example, a user can directly specify a short DNA sequence within the dna( ) function itself, e.g.,
myPrimer=dna("AAGTGTGAC").

Alternatively, the user may load from the library a DNA component by its ID or its name, using the dnaComponent( ) function:
plasmidBackbone=dnaComponent(13000109030) # Backbone referenced by a universal ID.
anotherBackbone=dnaComponent("my-backbone") # Another backbone, referenced by name.

As another alternative, a user may load from the library the DNA component that represents the sequence for a microbial strain, using the dnaForStrain( ) function:
aFamousSequence=dnaForStrain(7000000000) # Also accepts the strain name as an argument.

More generally, a DNA sequence may be identified explicitly (i.e., from a string), from a local source (file, database), or from a public source (e.g., NCBI).

DNA Specification

With reference to the DNA specification, the interpreter 204 also enables a user to identify DNA specifications, including, for example, by loading from the library an entire DNA specification, using the dnaSpecification( ) function:
somePrimers=dnaSpecification(18000000000) # The argument represents an identifier of the DNA specification.

This last example returns a DNA specification, whereas the previous examples returned a DNA component. Since both of these represent data of type DnaInput (the "supertype" of these two types), they are frequently interchangeable in DNA-modifying functions. That is, a program may create more complicated DNA specifications for campaigns by referencing either DNA components or DNA specifications as arguments. As will be discussed herein, even for complicated specifications, the DNA specification nevertheless provides a compact, human-readable data structure that enables the handling and creation of large numbers of sequences.

Note that the DnaInput value may be a DnaComp (DNA component; "DnaComp" and "DnaComponent" are used interchangeably herein to refer to variables or values of type "DnaComponent"), a DnaSpec (DNA specification; "DnaSpec" and "DnaSpecification" are used interchangeably herein to refer to variables or values of type "DnaSpecification"), a LocatedDnaSpec, a List[DnaComp] (a list of DNA components), or a List[DnaSpec] (a list of DNA specifications).)

Concatenation Function

The genomic design programming language and operations of embodiments of the disclosure support many different functions. As an example, Codon enables concatenation of DNA parts to make larger assemblies. Codon enables specification of individual sequences with DNA component functions such as dna( ), dnaForStrain( ) and dnaComponent( ). As an example when working with individual (scalar) values, Codon enables the concatenation of two scalar strings (using the "+" concatenation function) as follows:
left="left side"
right="right side"
combinedString=left+right LIMS, however, is particularly designed to design, build, test and analyze multiple DNA sequences at a time. Thus, Codon enables the user to work with lists of DNA sequences by, for example, loading a DNA specification (DnaSpec) that represents multiple DNA sequences with the function dnaSpecification( ). A program may create a DNA specification (DnaSpec) that represents a list of sequences by, for example, uploading to the library a file in known Genbank or CSV formats.

Concatenation of lists of sequences may be performed in at least two ways. If the lists are the same length, the DNA specification may specify concatenation of the items element-wise. Execution of the DNA specification by the interpreter 204 (or in other embodiments, the execution engine 207) would concatenate [a, b, c] and [d, e, f] as ad, be, cf. This function is denoted a "dot product." Alternatively, the DNA specification may specify concatenation of lists of any lengths via their Cartesian cross-product product to concatenate all possible pairs. Using the same example lists, the interpreter 204 (or in other embodiments, the execution engine 207) would concatenate the cross-product outputs as ad, ae, af, bd, be, bf, cd, ce, and cf. These outputs may be expressed as DNA components. As described herein, if the cross product would result in a very large number of outputs relative to memory capacity, the system 200 may employ sampling to reduce the number of outputs produced. As described further below, different sampling techniques may be employed, including weighting sample sets to include gene parts that have been determined during prior build and test cycles to have produced or influenced beneficial phenotypic properties. The order placement engine 208, then creates a factory order based on the outputs.

Codon represents the concatenation function in different ways. The concat( ) function will take two DnaInput arguments and concatenate the elements. The function includes a function modifier [*] or [x] between the function name and the argument list to indicate whether it is dot or cross product, as in the example below:
left=dnaSpecification(18000000001)
right=dnaSpecification(18000000002)
dotProducts=concat[*](left, right)
crossProducts=concat[x](left, right)

Because DNA concatenation is so similar to string concatenation, something that is typically done using math-like binary operators in modern programming languages, Codon offers a shorthand for concatenation: using the * or x directly to indicate concatenation, as shown in the following example.
left=dnaSpecification(18000000001)
right=dnaSpecification(18000000002)
dotProducts=left*right
crossProducts=leftxright
moreDna=dnaSpecification(18000000003)
You can use ( ) together with * or x to indicate associativity, which may affect
build order.
bigCrossProduct1=leftx(rightxmoreDna)
bigCrossProduct2=(leftxright)xmoreDna
You can also make associativity explicit with multiple statements. Note that default operators of equal precedence will be evaluated left-to-right. (e.g., bigCrossProduct2 expresses the default.)
The following is equivalent to bigCrossProduct1:
compoundRightSide=rightxmoreDna
bigCrossProduct3=leftxcompoundRightSide Recursion Referring to FIG. 3, the following is an example of implementation of a recursive concatenation function enabled by embodiments of the disclosure. Here, recursion refers to the organization of information or functions in levels or layers, where objects contain other similar objects, or the evaluation of a function depends on evaluation of other, similar sub-functions. In this example, the concatenation function, as well as the DNA specification, is recursive.

Before circularization of the output "total" below into plasmid form, the example function in linear form may be expressed as:
total=(p1×p2)×(p3×p4)
total=alpha×beta,
where alpha=p1×p2 and beta=p3×p4, and p1, p2, p3 and p4 represent promoters.

Here, the cross product concatenation of alpha and beta is the outer function, where each of alpha and beta represents an inner cross product of two promoters. Note that any of the inputs to the cross product function can be a list of inputs and not just a single input.

To implement this functionality in the programming language of embodiments of the disclosure, the input interface 202 may receive from the user or another computing device the following script. (In the code below, total is renamed "myplasmid" after circularization, and alpha and beta are, respectively, renamed "left side" and "right side." Thus, my plasmid=circularized (left side×right side).) Also, note that comments in program code may be represented by either "//" or "#" herein.

```
p1 = [ dna("AAA"), dna("AAG"), dna("AAT"), dna("AAC") ] // a
list of promoters, here each represented by a literal string
representing three nucleotides
p2 = dna("TT") // a single (scalar) string representing a
promoter
p3 = [ dna("CCA"), dna("CCC"), dna("CCG"), dna("CCT") ] // a
list of promoters
p4 = dna("GG") // a single promoter
setparam "name", "left side" // Assigns the string value "left
side" to the name parameter of the DNA specification that
follows setparam ("alpha").
setparam "leftTailLen", 25 // Sets the maximum left tail length
of alpha to 25 base pairs for PCR amplification at the factory.
alpha = p1 x p2 // alpha is cross product of p1 and p2
setparam "name", "right side" // Assigns beta the name "right
side."
setparam "leftTailLen", 50 // Set left tail length of beta to
50 base pairs.
beta = p3 x p4 // beta is cross product of p3 and p4
setparam "name", "my linear seq" //Assigns total the name "my
linear seq"
total = alpha x beta // total is cross product of alpha and
beta, which themselves are each cross products
setparam "name", "my plasmid" // Assigns the name value "my
plasmid" to the output of the circularized version of total
out = circularize(total) // circularizes the linear total
string into a plasmid representation
create out // specifies that "out" represents a design campaign
```

In this example, the interpreter 204 would populate the DNA specification with the function/operator, inputs and parameters, but would not execute the function to resolve the outputs. The resulting DNA specification "my plasmid" follows below, and is illustrated as a tree data structure 350 in FIG. 3. Note that the myplasmid DNA specification data structure is recursive, including child DNA specifications ("Child DnaSpec"), and that the child DNA specifications, in this example, include DNA components representing the input sequence operands.

```
DnaSpecification:
  Id: 18000000498
  Name: my plasmid
  Description: circularize
  Creating app: codon 1.0.0-SNAPSHOT-
477743830d11c9b0fbfaa80cd0ad98c7bc3547ba( )
```

```
Sequence Function: CIRCULARIZE (UNARY) // top-level function
(352) (reference numerals refer to Figure 3 tree data
structure)
    dnaInputs:
        items:
            Child DnaSpec: id=18000000497 {
                DnaSpecification:
                    Id: 18000000497
                    Name: my linear seq
                    Description: cross product concatenation
                    Creating app: codon 1.0.0-SNAPSHOT-
477743830d11c9b0fbfaa80cd0ad98c7bc3547ba( )
                    Sequence Function: CONCATENATE (CROSS) // (354)
                    dnaInputs:
                        left: // "left side" = cross product of list [AAA,
AAG, AAT, AAC] × TT
                            Child DnaSpec: id=18000000496 {
                                DnaSpecification:
                                    Id: 18000000496
                                    Name: left side
                                    Description: cross product concatentation
                                    Creating app: codon 1.0.0-SNAPSHOT-
477743830d11c9b0fbfaa80cd0ad98c7bc3547ba( )
                                    Sequence Function: CONCATENATE (CROSS) //
(356)
                                    dnaInputs:
                                        left: // the list [AAA, AAG, AAT, AAC],
represented by DNA component literal strings
                                            DnaComponents:
                                                DnaComponent: id=13000119900 {
                                                    DnaComponent:
                                                        Id: 13000119900
                                                        Name: dna string
                                                        Description: literal: AAA
                                                        Molecular form: LINEAR
                                                        Sequence: AAA
                                                }
                                                DnaComponent: id=13000119899 {
                                                    DnaComponent:
                                                        Id: 13000119899
                                                        Name: dna string
                                                        Description: literal: AAG
                                                        Molecular form: LINEAR
                                                        Sequence: AAG
                                                }
                                                DnaComponent: id=13000119898 {
                                                    DnaComponent:
                                                        Id: 13000119898
                                                        Name: dna string
                                                        Description: literal: AAT
                                                        Molecular form: LINEAR
                                                        Sequence: AAT
                                                }
                                                DnaComponent: id=13000119897 {
                                                    DnaComponent:
                                                        Id: 13000119897
                                                        Name: dna string
                                                        Description: literal: AAC
                                                        Molecular form: LINEAR
                                                        Sequence: AAC
                                                }
                                        right: // the scalar TT
                                            DnaComponents:
                                                DnaComponent: id=13000119896 {
                                                    DnaComponent:
                                                        Id: 13000119896
                                                        Name: dna string
                                                        Description: literal: TT
                                                        Molecular form: LINEAR
                                                        Sequence: TT
                                                }
                                    Parameters:
                                        leftTailLen: 25
                            }
                        right: // "right side" = cross product of list
[CCA, CCC, CCG, CCT] × GG
                            Child DnaSpec: id=18000000495 {
                                DnaSpecification:
                                    Id: 18000000495
                                    Name: right side
                                    Description: cross product concatentation
                                    Creating app: codon 1.0.0-SNAPSHOT-
477743830d11c9b0fbfaa80cd0ad98c7bc3547ba( )
                                    Sequence Function: CONCATENATE (CROSS)
//(358)
                                    dnaInputs:
                                        left: // the list [CCA, CCC, CCG, CCT]
                                            DnaComponents:
                                                DnaComponent: id=13000119895 {
                                                    DnaComponent:
                                                        Id: 13000119895
                                                        Name: dna string
                                                        Description: literal: CCA
                                                        Molecular form: LINEAR
                                                        Sequence: CCA
                                                }
                                                DnaComponent: id=13000119894 {
                                                    DnaComponent:
                                                        Id: 13000119894
                                                        Name: dna string
                                                        Description: literal: CCC
                                                        Molecular form: LINEAR
                                                        Sequence: CCC
                                                }
                                                DnaComponent: id=13000119893 {
                                                    DnaComponent:
                                                        Id: 13000119893
                                                        Name: dna string
                                                        Description: literal: CCG
                                                        Molecular form: LINEAR
                                                        Sequence: CCG
                                                }
                                                DnaComponent: id=13000119892 {
                                                    DnaComponent:
                                                        Id: 13000119892
                                                        Name: dna string
                                                        Description: literal: CCT
                                                        Molecular form: LINEAR
                                                        Sequence: CCT
                                                }
                                        right: // the scalar GG
                                            DnaComponents:
                                                DnaComponent: id=13000119891 {
                                                    DnaComponent:
                                                        Id: 13000119891
                                                        Name: dna string
                                                        Description: literal: GG
                                                        Molecular form: LINEAR
                                                        Sequence: GG
                                                }
                                    Parameters:
                                        leftTailLen: 50
                            }
                    Parameters:
                        leftTailLen: 50
            }
    Parameters:
        leftTailLen: 50
```

Assuming no sampling, the execution engine 207 would execute the DNA specification cross product operators on the operands to produce the following 16 sequences (which may be represented as DNA components). A sequence listing is provided with this disclosure.

| | | |
|---|---|---|
| AAATTCCAGG | SEQ ID NO: | 1 |
| AAATTCCCGG | SEQ ID NO: | 2 |
| AAATTCCGGG | SEQ ID NO: | 3 |
| AAATTCCTGG | SEQ ID NO: | 4 |
| AAGTTCCAGG | SEQ ID NO: | 5 |

| | |
|---|---|
| AAGTTCCCGG | SEQ ID NO: 6 |
| AAGTTCCGGG | SEQ ID NO: 7 |
| AAGTTCCTGG | SEQ ID NO: 8 |
| AATTTCCAGG | SEQ ID NO: 9 |
| AATTTCCCGG | SEQ ID NO: 10 |
| AATTTCCGGG | SEQ ID NO: 11 |
| AATTTCCTGG | SEQ ID NO: 12 |
| AACTTCCAGG | SEQ ID NO: 13 |
| AACTTCCCGG | SEQ ID NO: 14 |
| AACTTCCGGG | SEQ ID NO: 15 |
| AACTTCCTGG | SEQ ID NO: 16 |

Figure 3:
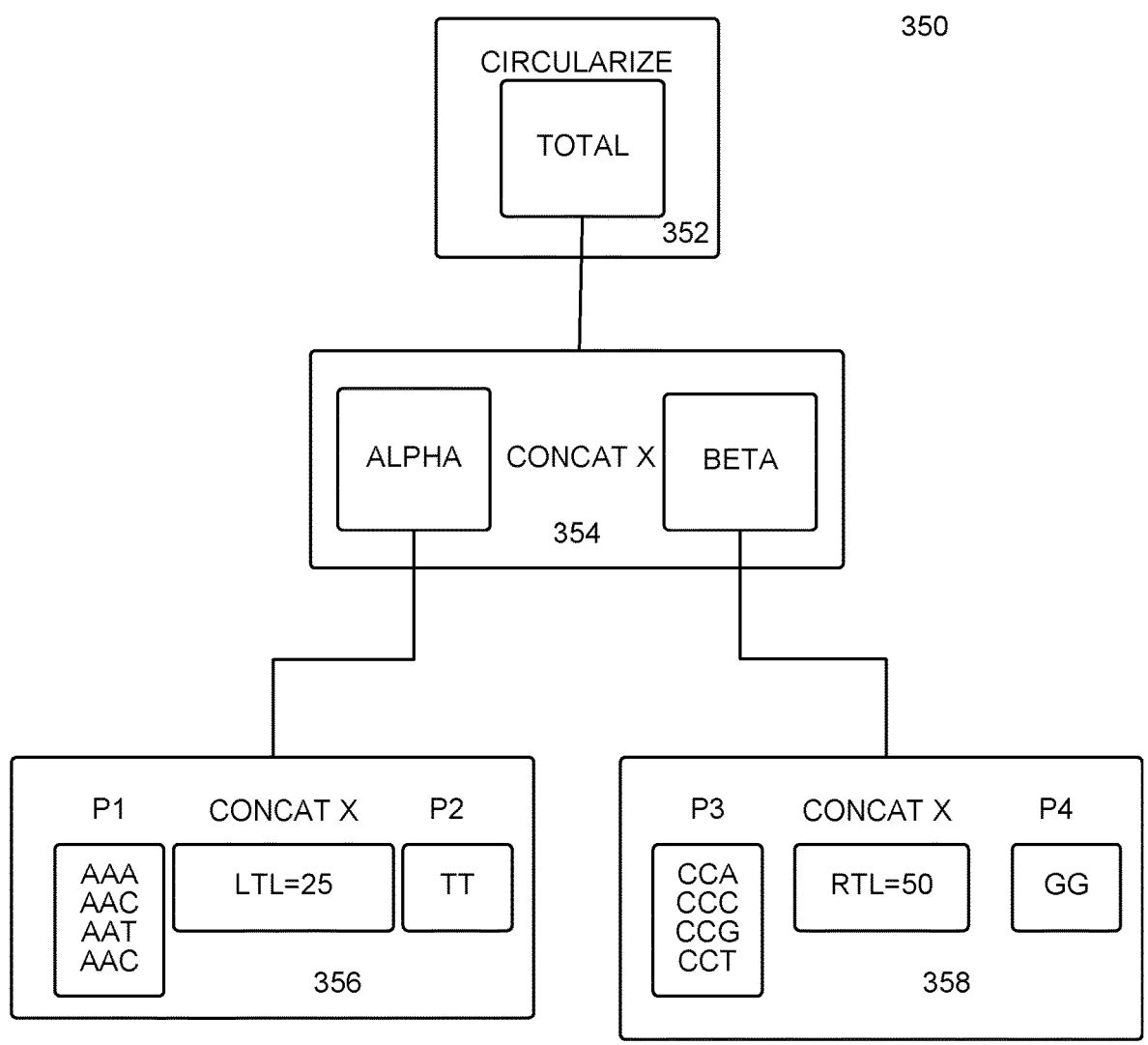
FIG. 3 illustrates an example of a recursive concatenation function enabled by embodiments of the disclosure.

An advantageous feature of embodiments of the disclosure is that the order placement engine 208 may employ the DNA specification data structure, such as that above, to inform its generation of a factory order beyond merely providing output nucleotide sequences for the factory 210 to produce. As noted above, the data structure is in the form of a tree, as illustrated in FIG. 3. The order placement engine 208 may traverse the tree structure from the leaves (e.g., leaf nodes corresponding to 356, 358) to the branches to the root node (e.g., corresponding to 352) to determine the operations performed at each stage of execution, as well as the inputs, factory workflow and other parameters employed at each stage. The order placement engine 208 may incorporate this information into the factory order. (Note that the "performance" of operations herein may alternately refer to in silico execution of the operations by the execution engine 207 or the interpreter 204 (depending upon the embodiment) or corresponding physical in vivo or in vitro physical reification of the operations in the gene manufacturing system, depending upon the context of the discussion herein, as would be recognized by those skilled in the art. For example, a concatenation operation on two nucleotide sequences would be performed logically by a computer device, whereas it would be physically reified by the joining together of two physical sequences in the factory.)

Thus, unlike conventional sequence design implementations, embodiments of the present disclosure provide a data structure for sequence design that informs the factory order placer (here the order placement engine 208) of not just the final sequence output, but also operational and contextual information at beginning, intermediate and ending stages of design development. The carrying forward of this information relieves the burden on the factory 210 to determine all beginning and intermediate parts, workflows and other parameters, thus improving the efficiency of production of the desired sequences. For example, based on this information in the DNA specification, the order placement engine 208 may determine the initial base strain to be modified, as well as potentially different promoters, workflows, temperature settings, and primers to be used at the factory 210 at different intermediate stages in the process of assembling the final, desired nucleotide sequence. For example, the tolerated range of annealing temperatures may be different for amplifying from genomic DNA than for amplifying from plasmid DNA.

Figure 4:
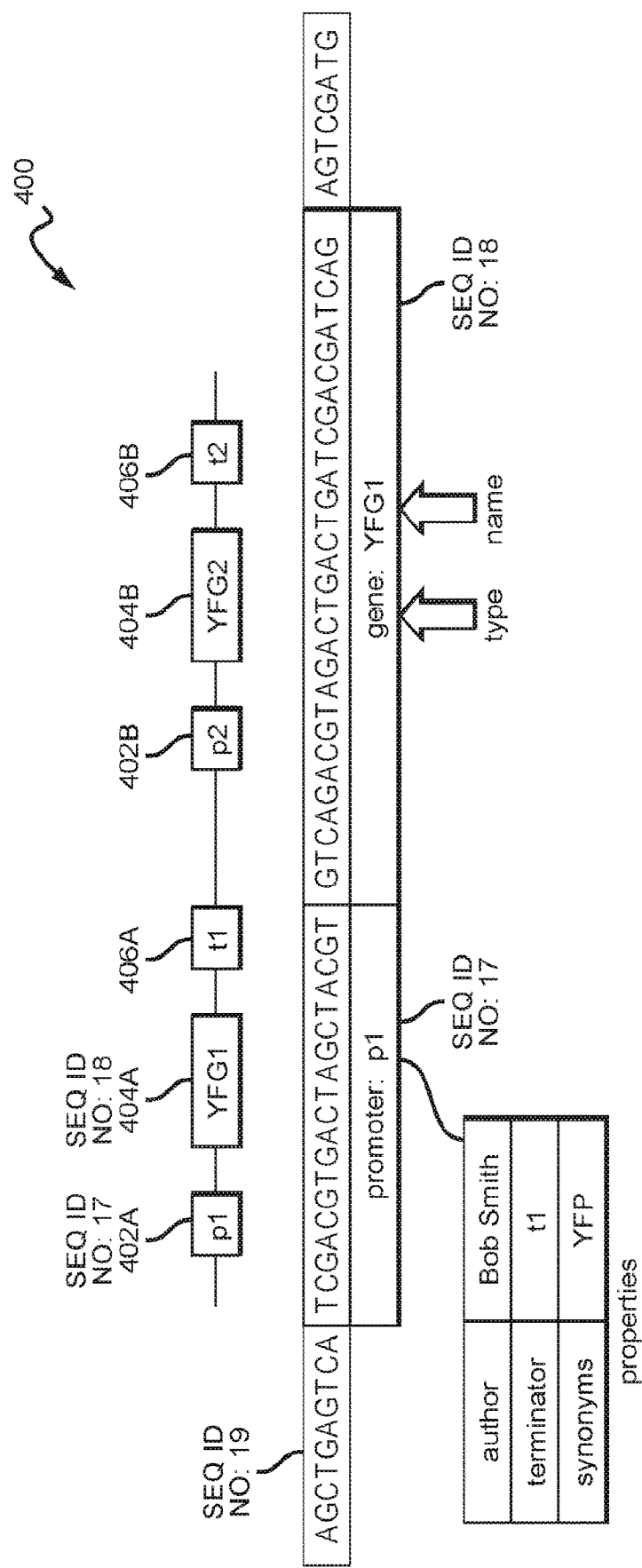
FIG. 4 illustrates an example of an annotated DNA sequence including two sets of promoters, genes, and terminators, according to embodiments of the disclosure.

The setparam keyword in the DNA specification may be used to set the name and description of any created DNA specifications, as well as other attributes governing how the factory operations are to be performed. The setparam statement takes two arguments, a parameter name, and a value to assign to it. Some parameters use a single string value; others can use a single string or a list of strings. The "name" and "description" parameters will set the most obvious user-visible properties of a DnaSpec. The following is a non-exhaustive list of parameters that can be specified using setparam:

amplifyPart—A boolean value of "true" or "false" to specify whether the part should be amplified.
assemblyMethod—The construction method to use at the factory to assemble the constructs. E.g., one of "yeast homologous recombination", "gibson", or "LCR"
description—The description to assign to the DnaSpec/campaign.
groupName—The name to assign to the collection of assembly parts produced by a particular DnaSpecification. May be used in conjunction with amplifyPart.
leftTailLen and rightTailLen—Integer values specifying the maximum tail length to generate for amplification
name—The name to assign to the DnaSpec/campaign.
notes—A longer free-form set of notes about the campaign for human reference. This may be a list of strings.
outputName—A string or list of strings specifying the names to assign the DnaComponents that are generated by the DnaSpec created with this parameter name. (e.g., if you are circularizing a set of inputs, you can setparam "outputName", ["myCircular1", "myCircular2", . . . ] to name the different circularized constructs.
primerSource—E.g., one of "IDT" (Integrated DNA Technologies, Inc.) or "library", to specify the source of primers for a campaign
plasmidSource—E.g., one of "build" or "library" to specify source of plasmids for a campaign
targetAnnealingTemperature—The desired temperature to be employed at the factory to amplify a construct Replacement Function Another particularly pertinent function is the replacement function. As an example of a program to replace the promoters located before genes in the DNA sequence of a microbial strain, refer first to the DNA component of FIG. 4. FIG. 4 illustrates an example of an annotated DNA sequence 400 including two sets of promoters 402A, 402B, genes 404A, 404B, and terminators 406A, 406B (generically "p-g-t" sequence), respectively p1 (SEQ ID NO: 17)-YFG1 (SEQ ID NO: 18)-t1 and p2-YFG2-t2. (Annotation is shown for promoter p1 (SEQ ID NO: 17) and gene YFG1 (SEQ ID NO: 18).)

Figure 5:
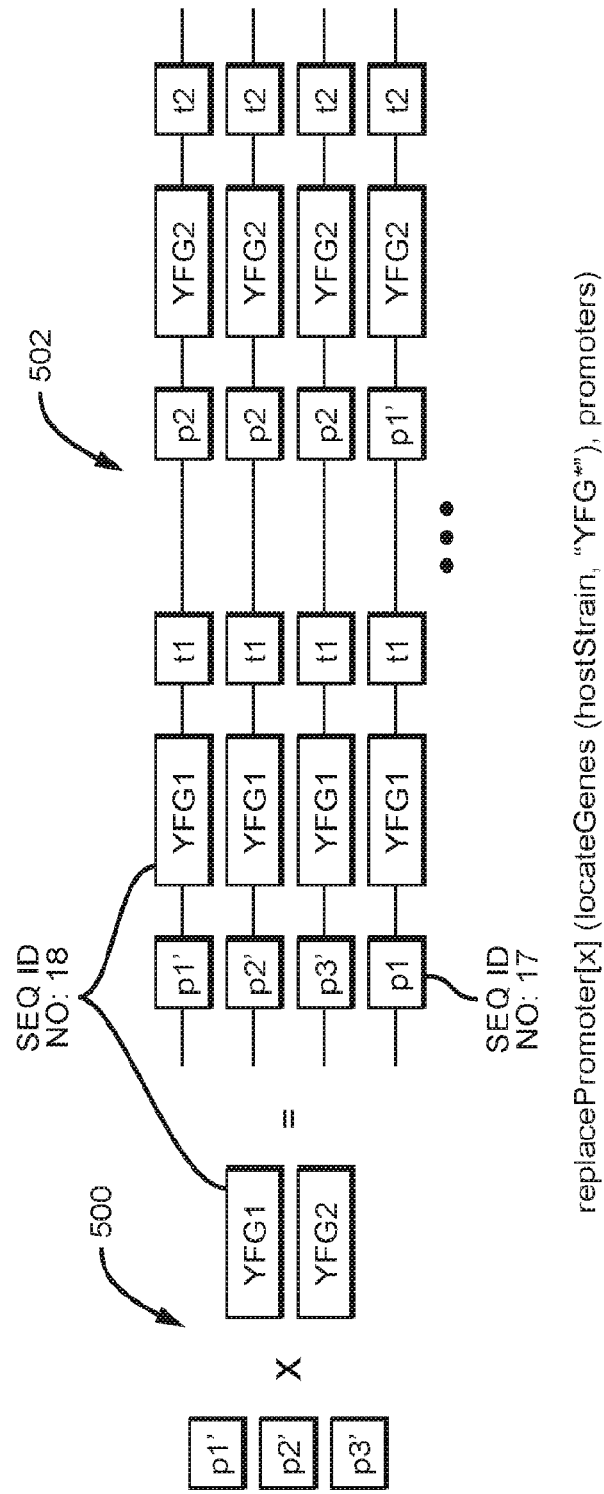
FIG. 5 illustrates a promoter swap operation applied to the sequence of FIG. 4, according to embodiments of the disclosure.

FIG. 5 illustrates a promoter swap operation 500 applied to the p-g-t sequence of FIG. 4. Using the combinatorial cross-product ("x") operation, the program will generate all combinations of all p-g-t sequences with the promoters in the original p-g-t sequence replaced one-by-one with p1', p2' and p3', resulting in six output sequences to be converted into a design campaign. (The first four output sequences 502 are illustrated in the figure.)

The program code for performing this operation follows. Descriptions of the functions are given in the comments.

```
hostStrain = dnaForStrain(
    "e-coli-461") # Load the DnaComp associated with the strain
    with the specified ZId or name.
```

-continued

```
promoters = load("promoter-lib-2-13-2015.gb") # Load from the
LIMS library all promoters identified by the name in the
argument.
genes = locateGenes(hostStrain, "YFG*") # Locate the genes
whose names begin with "YFG" in the microbe strain identified
by hostStrain variable, and assign this Located
DnaSpecification the name "genes. ("YFG*" stands for "Your
Favorite Gene," a placeholder for a user's preferred
descriptive name within a particular application instance.)
create replacePromoter[x](genes, promoters)
```

The replacePromoter( ) function replaces the promoter annotated as regulating a given gene. As indicated by the cross-product function call modifier "x", replacePromoter( ) here generates representations of all annotations (locations in the genome) identified by "genes" with representations of the genes' annotated promoters replaced by representations of promoter sequences identified by "promoters." This create function generates a DnaSpecification with a "replace" function, and parameters indicating that it should be performed in "replace-promoter" mode, that one argument list is the promoters, and the other argument list is Located DnaSpecification (here "genes"), i.e., one or more DnaSpecifications whose function is "locate," and indicates the collection of genes by name whose promoters should be swapped. The "create" function creates a design campaign for input to the factory for generation of DNA sequences.

One feature of embodiments of the disclosure is that the genomic design language includes genome-aware edit operations. For example, the interpreter 204 (or in some embodiments, the execution engine 207) executes replacePromoter( ) to obtain knowledge of the location of the promoter annotated as regulating the gene in the p-g-t sequence. By reading the p-g-t sequence in the library, the interpreter 204 (or in some embodiments, the execution engine 207) identifies the appropriate promoter for each gene from its DNA component annotations, and then enables replacement of the promoter. See *BBF RFC* 108: *Synthetic Biology Open Language (SBOL) Version* 2.0.0, editors Bartley, et al., Jul. 31, 2015 (annotations).

Note that replacePromoter( ) does more than use promoter annotations to locate the promoter regulating a gene. It replaces the whole sequence from the upstream end of the annotated promoter to the start codon of the gene. If no promoter annotation exists for a gene of interest, the new promoter will be inserted before the gene. If there are annotations that overlap the region of the promoter, the method will warn the user or sometimes try to rectify the collision.

Figure 6:
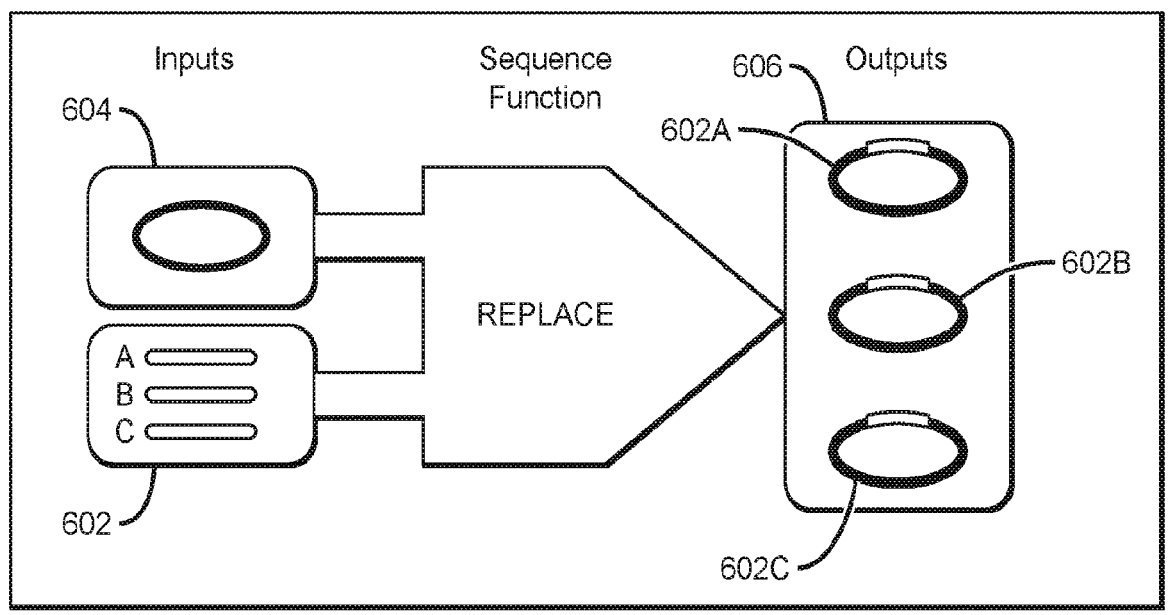
FIG. 6 provides a graphical representation of a DNA specification of a replace-locate cross-product function, according to embodiments of the disclosure.

FIG. 6 provides a graphical representation of a DNA specification of a replace [x](locateTerm[x](plasmids, "insertion-site"), newGenes) cross-product function for inserting genes (newGenes) 602A, 602B, 602C into a plasmid 604 by representing all three combinations 606 of the plasmid with its insertion region replaced with the specified genes 602A, 602B, 602C. The function takes the cross-product of the list of genes with the plasmid insertion region (which could be represented by a scalar DNA component) to output a DNA specification representing the modified plasmids. Alternatively, the plasmids may be represented as DNA components. The function first specifies the location within the plasmid of the sequence to be replaced by calling locateTerm[x] (plasmids, "insertion-site"). Alternatively, the insertion site may be located by identifying the name of the site location, e.g., locateName[x](plasmid, "MseI cut site"). These functions return LocatedDnaSpecifications. The replace function then performs the cross-product replacement of the list of newGenes into the locations specified by the LocatedDnaSpecifications.

The examples above demonstrate another advantage of the recursive capabilities of the programming language and data structures of embodiments of the disclosure. The language enables the user to independently control all stages of the sequence manufacturing process (beginning, intermediate, and end) by specifying the operations, inputs and conditions to be used at each stage of manufacture. In the example above, the specification specifies cross product operations at different levels (nodes) of the DNA specification tree structure: a cross product operation at the location resolution inner function, as well as at the replace function outer function further up the tree structure. Similarly, the user may have specified, at different stages/levels, different combinations of dot and cross operators, different parameters (e.g., temperature and other environmental conditions), and different inputs (e.g., promoters).

Non-Deterministic Functions

Embodiments of the disclosure provide probabilistic, non-deterministic functions, some of which reflect real-life results of laboratory methods that create stochastic results. In general, a probabilistic function effects changes to a nucleotide sequence in a non-deterministic manner. Examples are insertion of a transposable element at random locations of a sequence, one or more single nucleotide changes anywhere in the sequence (e.g. reflecting chemical or UV mutations), one single nucleotide change at the third position of any one codon in a coding sequence (e.g., through the production of an NNK library), one or two nucleotide changes at known locations (e.g., from PCR with degenerate primers), or an unknown set of changes via directed evolution. It follows that a non-deterministic operation on a biological component can lead to multiple mutated sequences.

The two examples below implement probabilistic functions enabling constrained randomization in the generation of nucleotide sequences.

```
# Define the starting sequence
enzyme_seq = dnaComponent(13000000000)
sequence_library = mutate(enzyme_seq, "NNK") # mutate the given
sequence using the NNK pattern (i.e., change the third base "K"
of each codon, with K restricted to a randomized selection of
either guanine (G) or thymine (T))
# Another example to create a degenerate primer
base_primer = dnaComponent(13000000001) # a template sequence
for the primer set
variable_locations = locate(base_primer, [4, 9]) # identify
positions 4 and 9 as those to vary
degen_primers = degenerate(variable_locations, ["A", "G", "C",
"T"]) # create the full set of possible primers whose base at
positions 4 and 9 could be any of A, G, C, or T selected
randomly.
```

Creating a Plasmid

As another example, the following program loads some promoters, some genes, a terminator and a plasmid backbone. Using the cross-product concatenation function, the program will create all possible combinations of promoters and genes (and the terminator), hook them each to the backbone, circularize them into a plasmid, and create a campaign that represents all these designs:

```
# Get the parts ready:
promoters = dnaSpecification(18000000001)
genes = dnaSpecification(18000000002) # id for YFG
# (a gene denoted by "your favorite gene (YFG)") goes here.
terminator = dnaComponent(13000000001)
plasmidBackbone = dnaComponent(13000109030)
# Create the P-G-T sequences. We want all possible combinations
of promoters and
genes, so we use the 'x' (concatenate cross-product) operator.
# Since we have only one terminator, and one backbone, and we
want them applied to all
sequences, we use 'x' again:
assemblies = promoters x genes x terminator
prePlasmids = assemblies x plasmidBackbone
# We don't want linear DNA, we want to circularize the
preplasmids to generate circular plasmids.
plasmids = circularize(prePlasmids)
# Specify that the 'plasmids' DnaSpec is the final campaign.
# This will upload the generated DnaSpec to LIMS.
create plasmids
```

Sampling

As discussed above, synthetic biology systems such as those of embodiments of the disclosure enable multiple operations to be performed on multiple DNA parts, represented by multiple DNA operands. Thus, the resulting design campaign may include representations of many thousands of DNA sequences. For example, a program may generate 10,000 modified genomes, which would occupy on the order of 50-100 GB of storage space. This information would not enable efficient management in a typical conventional memory at this time, and would instead require, for example, slower disk-based access. Current commercial computer systems cannot load and operate efficiently on a 50-100 GB SBOL file representing genomes. Such operations may crash or cause unacceptable delays in processing.

Embodiments of the disclosure avoid these potential storage and processing problems by sampling. In some embodiments, the order placement engine 208 may select only a subset of the outputs for incorporation into a factory order. This operation may employ many different techniques, such as, for example, random sampling to produce N constructs, or sampling the first or last K DNA constructs. To reduce storage requirements, this approach may store only the sampled outputs for incorporation into the factory order.

Alternatively, in embodiments in which the execution engine 207 executes the DNA specification to generate outputs that populate the DNA specification, the execution engine 207 itself may optionally sample the DNA specifications from the interpreter 204 to select a subset of DNA specifications for execution. This approach is particularly applicable to DNA specifications representing intermediate operations (e.g., child DNA specifications) within the larger, recursive DNA specification output data structure of the interpreter 204. As a result, the execution engine 207 produces outputs only for the selected, executed DNA specifications. Decoupling of interpretation by the interpreter 204 from execution by the execution engine 207 enables sampling-for-execution to reduce the size of the output by many orders of magnitude, thereby reducing the need for very large storage capacity and heavy processing.

The sampling operation of the embodiments immediately above may employ many different techniques, such as, for example, random sampling, or sampling the first or last K DNA specifications for execution. In addition, the execution engine 207 may more intelligently sample the DNA specification before execution. One approach is to weight DNA specifications for execution. For example, within the DNA specification data structure, promoters and other parameterized factors may be assigned different weights depending upon, e.g., their cost, availability, or known effectiveness. For example, assume a DNA specification data structure applies a concatenate cross product function to two input operands—a list of genes and a list of promoters. In this example, each promoter may be assigned weighting parameters (params) between 0 and 1 that would inform the execution engine 207 in its selection of DNA specifications to execute. The higher the weight of a promoter in the list, the more likely the execution engine 207 will execute the DNA specification for (apply the concatenate cross product operator to) such promoters.

The weights can themselves be added as parameters of a DNA specification to weight other parameters. For example, a child DNA specification (i.e., below the top-level DNA specification) may include a weighting parameter assigned a probabilistic weight expressed as weightPromoter=$p_i$ for a single promoter within the child DNA specification, or weightPromoter=[$p_1$, $p_2$, $p_N$] for a list of promoters within the same child DNA specification. The sum of the weights for the parameters (e.g., promoters) may add up to a value of 1, particularly for parameters at the same level of operations within the hierarchical tree structure of a recursive DNA specification.

Another strategy would be to employ a design-of-experiments methodology to intelligently select only a specified number of the possible promoter-gene combinations in order to learn the efficacy of each. As part of this implementation, the execution engine 207 may, in one embodiment, execute the appropriate specifications to ensure that each promoter is used at least once in a combination, while limiting the total number of combinations.

Even DNA components can be weighted to guide the execution engine 207 in its execution of operators on the DNA components. For example, a DNA specification having a list of DNA components as inputs may include a weight vector weightVector=[$p_1$, $p_2$, $p_N$] for the list of DNA components.

Caching

In embodiments of the disclosure, the execution engine 207 (or the interpreter 204 in embodiments in which the interpret executes DNA specifications) may employ caching to avoid the recalculation of results that may be re-used during execution of a DNA specification. For example, a specification may specify the cross product concatenation A×(B×C), where A, B, C are long lists of nucleotide sequences. The execution engine 207 would concatenate each element of A with all the elements resulting from the cross product B×C. It would be redundant and time consuming to recalculate B×C outputs for each concatenation with each item in A, so the execution engine 207 may instead cache those B×C results after the first computation of B×C, and then use those results in the cross product computations with the elements of A. Caching thus saves processing time and increases processing speed Caching finds use not just within the same run (e.g., generation of the order), but across different runs. For example, the user may determine that better or different results are desired compared to the sequences generated from a previous order. Accordingly, the user may re-run a program to place another factory order, perhaps this time directing sampling to select a different subset of DNA specifications to execute. In doing so, however, the script may still require execution of some of the same intermediate operations as prior order generation runs. With reference to the example herein of nested concatenation of right and left side promoters, a user may want to rerun the higher-level (total) concatenation function to obtain different right-side sequence outputs, but not change the left-side operations. Thus, the system may cache the lower-level, intermediate left-side results for later use during the re-running of the higher-level function. In general, outputs of lower-level operations (e.g., at the leaves (i.e, leaf nodes) of the hierarchical tree structure) would be needed more repeatedly than higher-level operations, so the execution engine 207 may favor caching lower-level outputs over those from higher levels if storage is constrained. Based on the foregoing, the execution engine 207 in embodiments of the disclosure caches DNA specification results from different levels of operations within the tree structure to avoid re-execution during subsequent runs, thus saving processing time and increasing processing speed.

Factory Build Graph

Order Placer Generation of Build Graph

According to embodiments of the disclosure, a factory build graph, representing a predefined factory manufacturing workflow, is an embodiment of a factory order. According to embodiments of the disclosure, the factory order placer 208 may accept a DnaSpecification describing, in abstract form, a collection of logical instructions to create one or more desired DNA designs, typically to be embodied within a microbe or other host cell. Depending on the particular physical requirements for implementing workflows in the factory, the order placer 208 may obtain, and indicate in the factory order, information indicating particular physical reactions and conditions. The order placer 208 may obtain this from the library 206, as it may be supplied by the user within the DNA specification (e.g., parameters such as reaction temperature).

Information concerning physical implementation of a workflow, as well as physical manufacturing parameters (e.g., primers, reaction temperatures) not already specified in the DNA specification, may be determined based upon physical workflows known in the industry, or proprietary to a developer, that have been developed through experimentation for synthesizing intermediate or final nucleotide sequences based upon given input sequences. This workflow is paired with a set of inputs that describe the work to perform in each step to manufacture each particular output design.

The Factory Build Graph may take the form of a data structure (see Appendix 2) holding a directed acyclic graph (DAG). The graph is a collection of records of two types, nodes and edges, along with zero or more properties. Each node has a node ID and tracks the edges emanating from it. Each node represents a nucleotide sequence (e.g., DNA) part, or cell strain, according to embodiments of the disclosure. These parts may be precursors (e.g., primers ordered from a third-party vendor), intermediate parts (e.g., longer DNA segments that are the result of concatenation, or plasmids used to integrate a change in a final strain DNA sequence), or the final DNA sequence, strain, or organism itself In embodiments of the disclosure, the order placement engine 208 traverses the DnaSpecification from the leaf nodes to the final root node (as described above), and uses each junction as an opportunity to compute how intermediate or final results at that level of the tree are created from prior dependency parts. The order placer 208 writes this information to the data structure of the DAG. This information is recorded in the context of particular workflow steps that would be used to physically perform the operation; therefore, in addition to recording the inputs and outputs of the step in nodes of the build graph, each edge is also annotated with a "role" that the source node plays in constructing a particular target. Nodes and edges in the data structure of the graph also hold other parameters as might be required to parameterize the workflow (e.g., temperature settings on a thermocycler being used in a PCR reaction).

Figure 8:
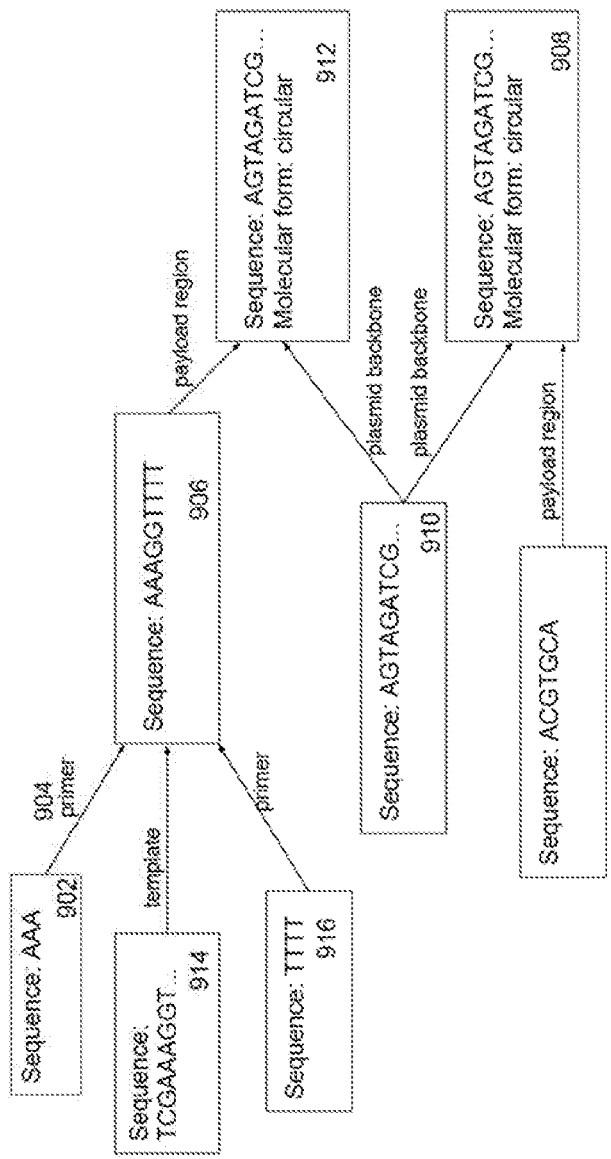
FIG. 8 illustrates an example of a factory build graph, according to embodiments of the disclosure.

The elements of the factory build graph are a combination of sequences or subsequences literally described in the DnaSpecification, as well as other sequences that are calculated by the factory order placement engine 208 itself—for example, primers used to amplify a particular subsequence of a longer template sequence in a PCR process, as illustrated in FIG. 8. In that case, the order placer 208 may represent the longer template sequence by a node of the graph. The order placer 208 may annotate the edge from this template sequence node to a node representing the PCR product with a role such as "template sequence." The order placer 208 may store the calculated primers in other nodes, and annotate their edges to the PCR product with roles such as "amplification primer." All of these nodes would have outbound edges to a fourth node representing the PCR-amplified subsequence.

In particular, FIG. 8 is a diagram of an example factory build graph. For brevity, this example is a partial build graph; a complete graph would contain all information from all root precursors to all final designs. In FIG. 8, a node 902 represents a DNA sequence. An edge 904 links the input DNA sequence of node 902 through a factory workflow process to an output DNA sequence of a node 906, specifying the role (in 904, "primer") of the particular input 902 in producing the particular output 906. The output sequence of node 906 includes the amplified sequence of the PCR process. Other nodes such as node 908 (computed by the order placement engine 208 or provided by the user) may contain further parameters and information required for physical or metadata processing of the sequence of node 908. Appendix 2 provides an example of a data structure representation of the top five nodes illustrated in FIG. 8 (node 1 902, node 2 914, node 3 916, node 4 906, node 5 912) in JSON serialization form).

In FIG. 8, the graph represents the sequence in node 906 acting in the role of a payload region, as indicated on the edge emanating from the node 906, to be concatenated with the sequence in node 910, which is shown as acting in the role of a plasmid backbone. The order placer 208 associates these two inputs with the physical manufacturing workflow of "concatenate payload region with plasmid backbone and circularize the result," as indicated in node 912. An operation supported by the order placement engine 208 is the ability to recognize when a particular precursor or intermediate sequence may be used in the manufacture of multiple desired output sequences being produced as part of the same order. The order placement engine 208 may represent such a sequence (for example, the common plasmid backbone 910) by a single node in the graph, with multiple output edges that lead to all intermediate or final sequences that directly depend on it. The order placement engine 208 may use this information to calculate volume, concentration or other quantities required to perform the manufacturing sub-workflows that correspond to the complete order. The number of outbound edges of a node can also be used by the order placement engine 208 to specify processing of the corresponding sequence in a different sub-workflow. For example, high-use amplicons may be processed via a different means than an amplicon that appears only once. Also, each path in the build graph is uniquely indexed and can be independently combined with other paths from different factory order build graphs. This construction allows a gene manufacturing system to assemble the sequence parts of multiple nucleotide sequences in a manner that is decoupled from the specific set of nucleotide sequences specified in a single factory order.

Workflow Engine Generation of Build Graph

As described above, the order placer 208 may generate the build graph. To do so, the order placer 208 has access to information concerning physical implementation of the workflow at the factory. Such physical implementation information may include temperature settings on a thermocycler being used in a PCR reaction, which may be obtained by the order placer 208 from a parameter specified in the DNA specification.

In other embodiments, however, the order placer 208 may not have access to information concerning physical implementation of the workflow at the factory. In that case, the order placer 208 may generate a factory order that specifies the workflow at a higher level, without detailed information concerning particular operations and operating parameters that may be best suited for manufacturing the product of interest at the factory based on the workflow. The factory order still may specify biological components, which may be represented by nodes in a build graph, to be combined to form other biological components, along with the relationships between the components, which may be represented by edges in the build graph. However, the build graph in these embodiments does not specify information (e.g., parameters) requiring knowledge of physical factory conditions and operations.

In particular for the embodiments described in this section and hereafter, the workflow engine, instead of the order placer 208, has access to information concerning physical implementations of workflows at the factory, and thus the workflow engine is used to generate the build graph. For the sake of convenience, some terminology particularly applicable to embodiments concerning workflow engine generation of the build graph is described below. Some terms are used for ordering the production of genetically modified strains, whereas others are more directed to the physical construction of the strains at the factory based upon the orders.

According to these embodiments of the disclosure, a "factory order" refers to a request to build one or more genetically modified microbes whose genetic modifications represent the application of one or more design techniques (e.g., promoter swap). Typically, a factory order refers to a request to apply one design technique to produce a modified microbe, which is then analyzed for performance. The analysis results are used in an iterative, feedback fashion through, e.g., the LIMS system of embodiments of the disclosure, to refine the sequence design and generate subsequent factory orders to optimize microbe performance.

According to these embodiments of the disclosure, the factory order includes specifications of genetic sequences to be incorporated into the microbes. The factory order may also specify one or more design techniques for producing the modified strain. The order placer 208 may determine reactions to implement specified design techniques (e.g., based on conventional knowledge of implementations that may be stored in library 206) to create the edges that can be used to make a build graph. The factory order may thus include information describing the edges, in which case the factory order may also provide identifications of intermediate DNA parts.

According to these embodiments of the disclosure, the factory order indicates sequence parts to be mixed together (e.g., a primer and a template) to make a new part, but does not specify further information on how to physically produce the modified microbe in the factory (e.g., the factory order does not indicate liquid transfer plans, assembly techniques, or reaction steps such as conjugation).

A "design technique" refers to the logical description of a method for modifying the genetic sequence of a microbe (e.g., promoter swap). In this context, a "logical description" refers to program code representing the manipulation of data (e.g., text strings) that itself represents genetic parts. The design technique and the organism being modified may influence the physical construction of the modified microbe.

A "workflow" refers to a sequence of workflow phases for physically constructing the modified nucleotide sequence specified in a factory order and incorporating that sequence into the organism being modified. According to these embodiments, a workflow is represented by a factory build graph.

A "workflow phase" refers to a sub-division of a workflow (e.g., parts generation, plasmid assembly, transformation). Based upon experimentation and industry experience, a workflow phase may be defined based upon the frequency with which different workflows share common implementations of the workflow phase, even though the overall workflows may be substantially different. A workflow phase produces an intermediate or final biological component.

"Reaction steps" refer to the individual physical reactions (e.g., PCR, electroporation) for implementing a workflow phase. The workflow reaction steps are to be distinguished from assay reaction steps described elsewhere herein.

A "protocol" refers to a collection of machine operations performed by one piece of automation equipment to effect a reaction step. For example, a liquid handling robot may execute a protocol to implement a liquid transfer to mix primers and templates on a plate to effect a PCR reaction set-up step, and a thermocycler may execute a protocol to cycle temperature to perform another PCR reaction step.

To clarify, unless otherwise indicated herein, the terms "microbial strain," "microbe," "cell," "biological component," or the like refers to a type of "microbial strain," "microbe," "cell," "biological component," or the like, respectively, and not to a respective, individual, isolated version thereof.

Figure 10:
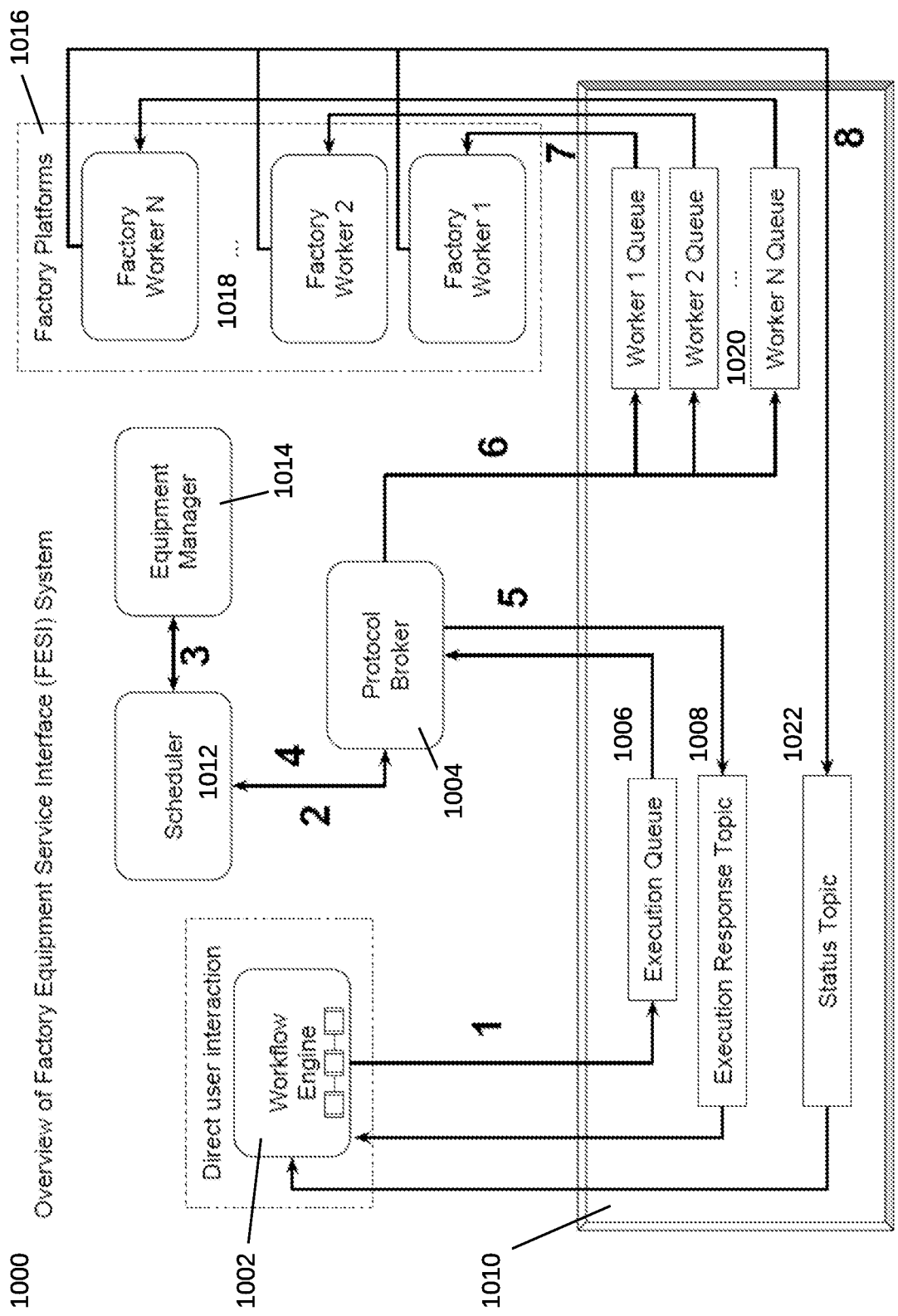
FIG. 10 illustrates a factory equipment service interface, according to embodiments of the disclosure.

Referring to FIG. 10, a factory equipment service interface (FESI) 1000, including workflow engine 1002, may reside at the factory 210 or be closely coupled to it. According to embodiments of the disclosure, the workflow engine 1002 has access (including real-time access) to information concerning physical implementation of the workflow at the factory. For example, the workflow engine may have real-time access to information concerning manufacturing capacity of particular pieces of factory equipment, as well as volumes of available reactants. That access may be obtained through communications with the factory (e.g., factory platforms 1016) or input by a factory operator. In these embodiments, the workflow engine 1002 would still receive a higher level factory order from the order placer 208, but the workflow engine 102 would perform the functions described elsewhere herein as being performed by the order placer 208 when the order placer 208 has access to information concerning physical implementation of the workflow at the factory, such as manufacturing capacity of particular pieces of factory equipment.

The FESI 1000, may reside within the factory 210 or be interposed between the order placer 208 and the factory 210, according to embodiments of the disclosure. The FESI 1000 includes a network for enabling communication between software and hardware elements. The workflow engine 1002 communicates messages with a protocol broker 1004 via an execution queue 1006 and an execution response topic exchange 1008 in a message bus 1010, a scheduler 1012, an equipment manager 1014, and factory platforms 1016. The factory platforms 1016 include factory workers 1018 that communicate with the protocol broker 1004 via corresponding worker queues 1020 in the message bus 1010 and with the workflow engine 1002 via a status topic exchange 1022, according to embodiments of the disclosure.

When a factory order is received by the workflow engine 1002, it may use knowledge concerning physical implementation of the workflow at the factory to determine the reactions to be performed at each workflow phase and the conditions required to achieve those reactions. This includes details on the inputs to each reaction (the reactants) and what is produced by each reaction (the reaction products). Since the reactions are in a sequence, the products of one reaction will very often become the reactants of a future reaction in the sequence. In embodiments of the disclosure, the workflow engine 1002 persists this knowledge in build graph relationships.

Those skilled in the art will recognize that, in other embodiments, the order placer 208 and the workflow engine 1002 may have access to factory physical implementation information to differing degrees, and thus each may use that information accordingly to allow both the order placer 208 and the workflow engine 1002 to contribute physical implementation information to the build graph.

Combining Sub-Workflows to Increase Operational Efficiency

As indicated above, biologists and others involved with designing strain edits ("Development Scientists") may use embodiments of the disclosure to specify a high-level biological workflow, including inputs and final products. Each completely specified workflow describes both edits (what to change) and steps (how to cause the edit to occur, biologically). For example, a workflow may specify the collection of plasmids and amplicons which will be used to introduce a particular edit into a strain. In embodiments, workflows may be specified using DNA specifications (see detailed description elsewhere herein). In order for the edits to be successfully applied to a strain, multiple steps of a biological workflow may be required. In embodiments of the disclosure, the workflow engine 1002 determines (e.g., by traversing the DNA specification data structure) the intermediate outputs required and the relationships between those outputs. In embodiments, the result of a particular workflow is a variant of an existing strain that incorporates some edits, as defined by the Development Scientist.

Workflows are modular and composable. To take advantage of operational efficiencies, the system (e.g., using the workflow engine 1002) of embodiments of the disclosure allows biologists involved with the physical production of components ("Factory Operators") to combine portions (sub-workflows) of several workflows. This combination is denoted a "cohort" and each particular piece of work is denoted a "line item." After the Factory Operator has created and selected a cohort to build, the workflow engine 1002 may create a corresponding build graph for that portion. In this context, the build graph is a data model that represents the instructions for building one or many line items in parallel.

Each biological component (e.g. plasmid, amplicon) is represented by a node in the build graph. As described previously, the build graph itself is a multi-edged, directed graph with labeled edges. It is directed so that it can answer questions about precedence. The labeled edges define the build relationships between the components (e.g. "primer"); each node is connected to another node in the graph by a directed edge.

Each "level" of the graph defines a collection of reactions needed to ultimately create a modified strain. A common build graph pattern is for leaf nodes in the graph to represent primers and templates, which produce amplicons, which produce plasmids, which produce a modified strain. The system represents these reactions as a series of nodes (components) and edges (roles in the reactions) in the build graph. A build graph has one "root" for each line item requested.

This construction means that build graphs are independently separable and recombinable from their roots. When a collection of build graphs—that is, a collection of line items, selected by Factory Operators because of operational convenience—shares common structure, that structure may be deduplicated as the workflow engine 1002 creates a single, unified build graph. In particular, this single build graph for a collection of line items combines the intermediate nodes when they are identical. In turn, identical intermediate parts need only be built once, and the system allows factory operations to take advantage of economies of scale.

According to embodiments of the disclosure, a typical work pattern is for the workflow engine 1002 to create and retrieve the build graph for a cohort. While the build graph data structure is defined by the nodes and their relationships to each other, it also provides the capability of answering specific operational questions about physical components. For example, using the build graph it is possible to ask and answer questions such as, "What are the primers associated with amplicon X?", even when amplicon X is used at several different steps of workflows that define several different strain edits.

Figure 9:
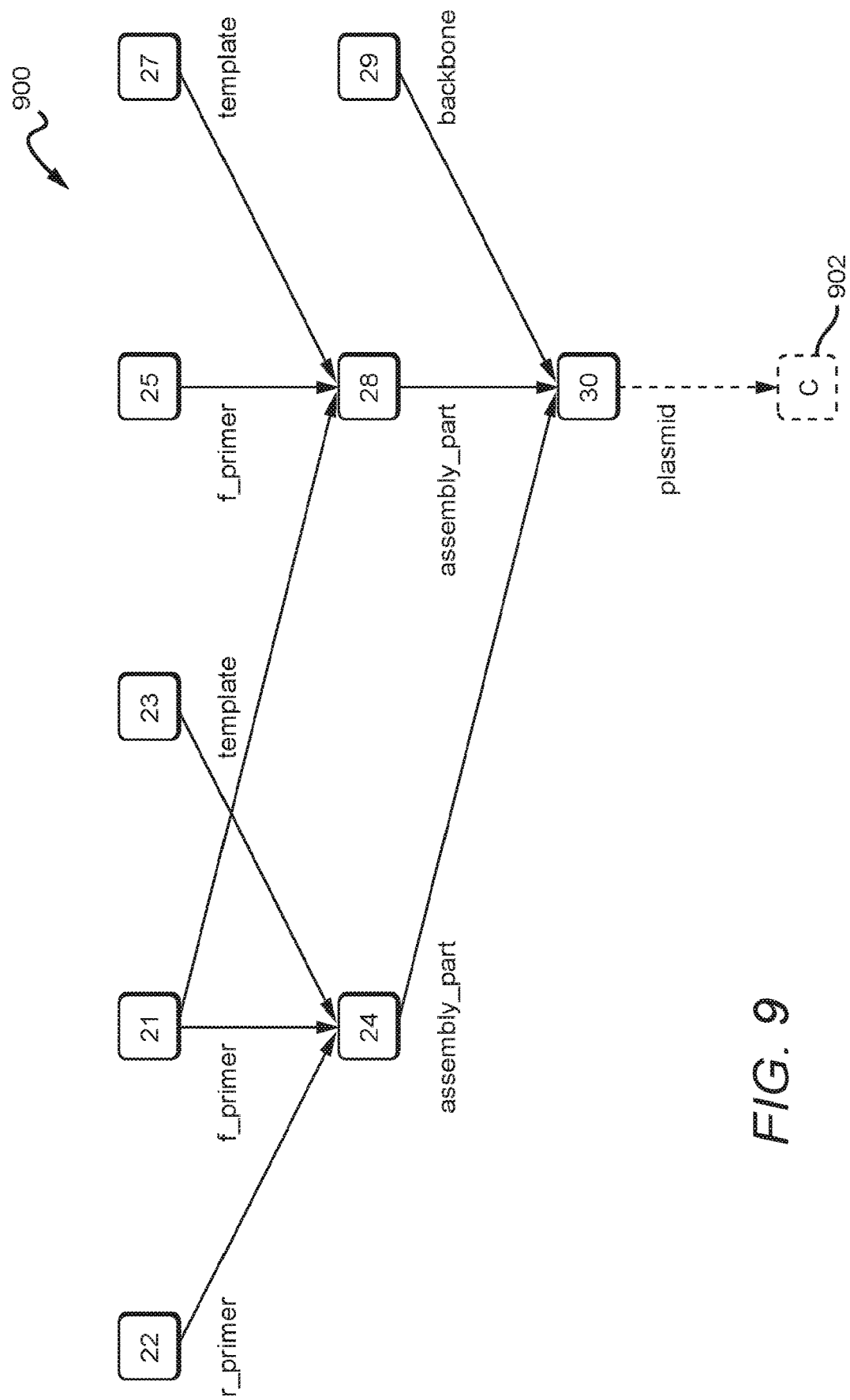
FIG. 9 illustrates another example of a factory build graph, according to embodiments of the disclosure.

FIG. 9 illustrates a build graph 900 for building one strain "C" 902. Particular components (e.g. node 21) have multiple build relationships, of different kinds (forward primer, reverse primer) with different components in the next, child level of the graph Planning Manufacturing Work from the Build Graph After the Factory Operator has selected work to perform and the workflow engine 1002 has created the build graph, the workflow engine 1002 traverses the build graph and maps each set of inputs and outputs both to physical laboratory equipment and to descriptions of biological protocols for each step in the workflow.

In this planning step, the workflow engine 1002 maps out the physical work. The workflow engine 1002 associates each level of the build graph with a plate role and plate mask. This association may be based on input from the Factory Operator. The plate role is a data model that describes the function of the plate, and is typically based on the directed edge coming into this level of the build graph (e.g. "primer"). The plate mask is a data model that describes how the physical layout of a typical laboratory plate relates to expected values, such as identifiers of particular designed (but not yet built) strains.

Plate masks for the final step ("product" plate masks, that is, for the plates that will contains the final, edited strains) are laid out by the workflow engine 1002, based on, e.g., input provided by the Factory Operator.

Plate masks for intermediate steps (e.g. "primer" plate masks) may be determined by the workflow engine 1002. To accomplish this, the workflow engine 1002 refers to the build graph. The workflow engine 1002 may also refer to the library 206 for relevant information such as the parameters for each reaction step and other physical implementation information represented by the build graph, or otherwise obtain such information from the factory 210.

In the example of primer plate masks, the workflow engine 1002 may determine, from the build graph, how many times a particular primer is used; this determines the number of wells (replicates) of the primer that are required.

Additionally, the workflow engine 1002 may determine the intermediate plate masks in a way that optimizes the efficiency of the physical work. For instance, a "stamp" operation (transferring liquids from positions in a source plate to the same corresponding positions in a destination plate, in the same geometry) is much faster than a liquid transfer operation from wells in a source plate to arbitrary well locations in a destination plate, which also may be of a different geometry. Thus, the workflow engine 1002 may determine and optimize the layout of the intermediate plate masks to allow for stamps instead of generic liquid transfers.

The workflow engine 1002 may design the layout of the plate mask to take into account known physical implementation information such as process variations. For example, if wells on the edges of a plate react less quickly for a given biological process on some equipment, the workflow engine 1002 can place the planned reactions appropriately. The combination of a plate role and system-determined plate mask can then be laid on top of any particular physical plate provided during execution of the automated workflow.

Based on the plate masks it has created, the workflow engine 1002 may determine and plan the exact liquid transfers required; this is referred to as a liquid transfer plan. For each level of the build graph, the plate mask for the destination plate describes the desired content (product) for each individual well. Using that product, the workflow engine 1002 uses the build graph to find the predecessors of the product (that is, what in the previous level of the build graph connects to this product? What are the reactants of this product?). Then, the workflow engine 1002 may search the source plate for wells containing the reactants, and matches those source wells to the destination wells for transfer.

Additionally, when searching the source plate, the workflow engine 1002 can take into account existing physical constraints known by the automation systems that are executing the manufacturing work. For example, the workflow engine 1002 can choose source wells based on known volumes of reactant available in those wells. These well-level matches between source plates and destination plates are then used to specify liquid transfers, which form the basis of instructions used in the FESI part of the system.

Executing Manufacturing Work from the Build Graph

After using the build graph to plan the manufacturing work, the system can communicate between the higher level descriptions of biological protocols (that is, the build graph and planned work) and the specific automated platforms that perform the individual steps of the protocols.

Referring to FIG. 10, the FESI 1000 is both device agnostic (can communicate with multiple types of platforms) and language agnostic (can communicate using multiple software languages), making it both modular and easily extensible to new platforms and protocols. There may be multiple automated platforms performing different steps of a given protocol. The system coordinates the scheduling of all of the interconnected platforms. A platform may include one or more pieces of automation equipment, and has its own connection to the network. A single platform type may have multiple instances, allowing for a given protocol to have multiple options as to where it may be run. A single platform may also be able to run multiple protocol types. The software used to interpret instructions and communicate with the rest of the system is known as a factory worker.

The message bus, comprising multiple queues and topic exchanges, communicates between the workflow engine and the factory workers. The messages comprise protocol buffer objects which can be compiled and decompiled to objects in most major programming languages, keeping the system programming language agnostic. The protocol broker is a software service that works as the go-between to direct the execution instructions from the workflow engine to an available factory worker that can execute the instructions. The protocol broker consults with the software scheduling service and the equipment manager to determine which platforms are available to run the protocol at a given time. The equipment manager maintains the set of all available platforms, protocols, and associated metadata, such as equipment state and protocol validation status. The separation of this data from the working logic of the protocol execution keeps the system agnostic to device and platform.

Because of the use of the message bus to communicate, the system is agnostic to the language and operating system of the workflow engine and the factory workers. In addition, it is not even required that all of the factory workers run on the same operating system or use the same language, as long as they have a connection to the network and can subscribe and publish to queues and topic exchanges.

FIG. 10 illustrates the flow of communication within the FESI 1000, according to embodiments of the disclosure. First, when the workflow engine 1002 determines that it is time to run a specific protocol (such as a liquid transfer plan), it publishes an execution request to the execution queue, which is picked up by the protocol broker. The execution request includes the protocol to be run, a unique identifier known as a request id, and any additional variables that the user may request, such as the amount of laboratory equipment to be acted upon. Upon picking up an execution request, the protocol broker communicates with the scheduler and in turn the equipment manager to determine which platform and factory worker is available to run the requested protocol (steps 2, 3, and 4 in FIG. 10). If no such factory worker is available, the protocol broker communicates this back to the workflow engine, and thus the user, by posting a message to that effect to the execution response topic exchange (step 5).

Once a factory worker is assigned by the protocol broker, the scheduler notes that it is in use and the protocol broker posts two messages: one to the execution response topic, to be read by the workflow engine indicating that the process has begun (step 5), and one to the assigned worker's worker queue requesting that the protocol begin including the request id from the original execution request (step 6). Each factory worker has its own worker queue from which it reads requests (step 7).

When a given factory worker receives a request on its queue, the worker translates the request into machine-specific instructions. These are used to run the protocol, incorporating any input values from the execution request. The factory workers publish all intervening status messages specific to the protocol, including measurements and status updates, to the status topic exchange along with the original request id (step 8). When the factory worker has finished executing the protocol, it publishes a final status message to the status topic exchange indicating completion of the protocol connected to the included request id. Using the request id, the workflow engine may connect these status messages with the specific workflow that made the request and move the entire workflow forward in response. The workflow engine can then request the next set of execution instructions, eventually receiving instructions for each of the steps in the high-level workflow specified in the build graph.

Factory Orders and Build Graph Creation

This section provides further details on the generation of build graphs, particularly the creation of build graphs for cohorts to improve manufacturing efficiency. A factory order defines a collection of strains to build, each incorporating a genetic edit. The factory order is placed by specifying a specific design technique that control the design. Because a particular strain can be ordered in more than one factory order, possibly using different design techniques, the workflow engine 1002 may create a line item for each strain ordered. A line item is an instance of ordering a particular strain, particular to a single factory order (and thus particular to the design technique employed in the factory order). Line items are useful because they record the association between a strain, an order, and the design technique used in the order.

For example, a factory order may be placed to construct a collection of strains using the promoter swap design technique, where a genome's promoter region (which influences the expression of one or more genes of interest) is swapped for another promoter to increase or decrease the expression of the corresponding target genes. To place such a factory order, a scientist may specify (e.g., via a DNA specification) as input the parent strains to be altered, the genomic regions to be replaced on the parent strain (the native promoter), and the genomic sequence to be used as a replacement (the new promoter).

The construction of strains carrying the genetic changes specified in a factory order requires a series of biological reactions. The design technique and type of organism used when placing the factory order determines the series of reactions, as well as the biological technology used for each reaction. For example, the workflow engine 1002 may determine that a single promoter swap design technique performed on a single strain may require the following workflow phases to be implemented by the following series of corresponding biological reactions:

Design technique: promoter swap (a) Workflow phase: Parts Generation. Reaction: PCR reaction to generate DNA parts that together encode a genetic sequence including the new promoter.

(b) Workflow phase: Plasmid Assembly. Reaction: Yeast homologous recombination, a reaction that stitches together the DNA parts from the previous step into a plasmid, which can be readily introduced into a strain.

(c) Workflow phase: Transformation. Reaction: Electroporation, a reaction in which plasmids are introduced into parent strains by using electricity to make the parent strains competent (capable of taking new DNA into their cell walls), and the cell's own genetic machinery is used to incorporate the plasmid DNA into the genome of the parent strain, producing the new, modified strain.

For the promoter swap design technique and some organism, the description above provides an example of a specific kind of reaction used for each workflow phase. Different design techniques, different organisms, or different performance requirements (efficiency, success rate) may necessitate different kinds of reactions at each workflow phase. For example, the workflow engine 1002 above has determined that the organism was susceptible to electroporation. In some cases this might not be the case, and the workflow engine may otherwise direct use of an alternative reaction type driven by a different biological technology. For example, Transformation may be accomplished via conjugation, a reaction which uses the machinery of a separate bacterium to incorporate a plasmid into the genome of a parent strain.

As discussed above, when a factory order is received by the workflow engine 1002, it may use knowledge concerning physical implementation of the workflow at the factory to determine the reactions to be performed at each workflow phase and the conditions required to achieve those reactions. This includes details on the inputs to each reaction (the reactants) and what is produced by each reaction (the reaction products). Using this knowledge, the workflow engine 1002 may determine, for any line item ordered, the specific series of reactions to execute to create the strain ordered by the line item. This includes details on the inputs to each reaction (the reactants) and what is produced by each reaction (the reaction products).

In embodiments of the disclosure, the workflow engine 1002 persists this knowledge as build graph relationships. A single build graph relationship represents a single edge that can be added to a build graph. Four pieces of data may define a build graph relationship:

(a) The ID of a reactant for a reaction (the source of the edge).

(b) The ID of the product for the reaction (the destination of the edge).

(c) The string identifier of the purpose of the reactant in the reaction that produces the product.

(d) The line item this relationship is relevant to building.

A single relationship on its own is not very useful (a single edge does not even completely specify a single reaction). However, since each relationship is indexed by the line item it is relevant to building, the workflow engine 1002 may analyze the factory orders for all the relationships relevant to building a particular line item, and those edges can then be dynamically combined into a build graph which completely specifies all the reactions required to construct the line item. Build graphs are useful because they completely specify the series of physical reactions needed to construct a line item, in a form that can be queried to actually execute those physical reactions.

The fact that individual relationships are stored in this way also means that build graphs can be constructed for arbitrary collections of line items. This knowledge can be exploited using a cohorts, each of which is a manufacturing unit of work that enables better utilization of the factory's manufacturing capacity.

Different factory orders may lead to the use of different reaction types for a particular workflow phase, but may also share the same reaction types in other workflow phases. Returning to the example above, consider the two factory orders, both using the promoter swap design technique, but one using an electroporation-susceptible organism and one using a conjugation-susceptible organism for the Transformation phase. In the workflow phase Parts Generation, line items from both orders would use the PCR reaction. Thus, at that stage of the construction process, line items from the two orders may be processed together. In the later workflow phase Transformation, the orders use different reactions (electroporation and conjugation), and so line items from the two factory orders cannot be processed together and must be worked on separately.

If the manufacturing capacity for Parts Generation (using PCR) is higher than the number of line items likely to belong to a single factory order, it is advantageous to be able to work on line items from multiple factory orders together so that the manufacturing capacity can be fully utilized. For this reason, the concept of a cohort is useful. A cohort is defined as a grouping of line items that may be worked on together at a particular workflow phase. The line items can come from any factory orders (even factory orders employing different design techniques and organisms). Cohorts are the manufacturing unit of the factory. A cohort can be filled with line items until the manufacturing capacity associated with a particular workflow phase is realized. Cohorts are useful because they allow for the arbitrary grouping of work at particular stages of the manufacturing process, in the way that best utilizes manufacturing capacity by taking advantage of commonalities in process between different factory orders.

Since a cohort is, in part, defined by the line items in the cohort, the workflow engine may dynamically construct the build graph for a cohort by querying for the build relationships relevant to all line items in the cohort. The knowledge in this graph can then be used to plan and execute the liquid transfers required to perform the physical reactions needed at the workflow phase the cohort pertains to (as detailed above). Another advantage of the build graph is this ability to construct and use a build graph for any grouping of line items (e.g. cohort). This grants great flexibility in what bodies of work the manufacturing system can be applied to.

Quality Control in High-Throughput Strain Design Systems

QC Test Design

Embodiments of the disclosure may employ elements of the LIMS system of FIG. 1 or similar elements separate from the LIMS system to design a quality control test representing one or more assays to be performed on intermediate and final biological components corresponding to reaction steps in the generation of a product of interest in the factory 210. Such assays may include, without limitation, restriction enzyme digest, PCR, growth assays, optical density readings, and DNA quantification.

According to embodiments of the disclosure, an input interface, such as that of interface 202, receives statements of a program/script that specifies the quality control test, which itself comprises one or more assays. As noted elsewhere herein, the input interface may allow for direct user input or input from another computing device via an API.

According to embodiments of the disclosure, an interpreter or compiler/execution unit like that of unit 204 or unit 207, respectively, evaluates program statements into data structures for quality control testing. According to embodiments of the disclosure, based upon the specified quality control test, the execution engine 207 selects the assays to perform the QC test. The execution engine 207 may access the library 206 to search for appropriate assays based upon the specified QC test. According to embodiments of the disclosure, the order placer 208 determines expected results of the assays for the target biological components based on, e.g., expected assay reaction products and reference information stored in the library 206.

According to embodiments of the disclosure, the QC test functions performed by the execution engine 207 and the order placer 208 may be performed by the workflow engine 1002. For the sake of convenience, the software portions of the one or more modules (e.g., execution engine 207, order placer 208) involved in designing quality control tests shall be referred to herein as the "QC test design engine."

According to embodiments of the disclosure, instead of just looking up expected assay results for target biological components based on, e.g., expected assay reaction products and reference information stored in the library 206, the QC test design engine can compute some or all of that information in real time. For example, given a plasmid as a target biological component and an enzyme as a reactant, the QC test design engine may in silico search the plasmid for instances of the enzyme's recognition site (e.g., AGGA). From that site information, the QC test design engine can derive the number and sequence of parts (nucleotides) between recognition sites, which serves as reference information for the QC test.

The data structure may be in the form of a directed graph, as described elsewhere herein. The test equipment 212 transforms the QC data structure from a logical specification into a physical QC process, according to embodiments of the disclosure.

According to embodiments of the disclosure, the QC test design engine is used for designing quality control testing on a plurality of biological components. According to embodiments of the disclosure, the QC test design engine (1) performs, in silico, one or more assays on one or more target biological components, where the in silico performance of each assay on one of the one or more biological components produces one or more assay reaction products (e.g., multiple plasmid fragments) resulting from an assay reaction (e.g., digestion) involving the one of the one or more target biological components (e.g., a plasmid); (2) classifies two or more expected outcomes of each assay as being from the group of: at least one success mode or at least one failure mode, based at least in part upon empirical information concerning the assay; and (3) stores, in an assay data structure, for the one or more assay reaction products, reference information including: (a) attributes of the one or more assay reaction products, and (b) the classification of the two or more expected outcomes.

According to embodiments of the disclosure, the test equipment 212 processes the assay data structure by: (a) instructs laboratory equipment to perform one or more physical assays, corresponding to the one or more in silico assays, on the one or more target biological components using physical laboratory equipment to generate one or more physical assay reaction products for each physical assay; and (b) for each physical assay, comparing the one or more physical assay reaction products to corresponding reference information to classify the target biological component as corresponding to the at least one success mode or the at least one failure mode.

The target biological components may comprise a plasmid, and the one or more reaction products may comprise plasmid fragments. Each target biological component may comprise a nucleotide sequence or a microbial strain.

The empirical information concerning the assay may comprise empirical information concerning the one or more assay reaction products. Classifying may be based at least in part upon the assay reaction, an assay reactant involved in the assay reaction, and the one of the one or more target biological components. Performing, in silico, one or more assays on one or more target biological components may comprise performing, in silico, at least two assays of the one or more assays on a first target biological component of the one or more target biological components.

The assay data structure can be a directed graph that includes, for the one or more assays on the one or more target biological components, a plurality of levels including a plurality of assay nodes. According to embodiments of the disclosure, in the directed graph, each assay node that resides at a level of a plurality of levels represents one of the one or more of the target biological components, one or more assay reactants, or one or more of the assay reaction products; a target assay node of the plurality of assay nodes represents, at a given level, a target biological component of the one or more target biological components; and an assay reaction product node, of the plurality of assay nodes, that is associated with the target assay node, represents, at a child level of the given level, the one or more assay reaction products and the reference information.

According to embodiments of the disclosure, the given level includes at least one assay reactant node representing at least one assay reactant that reacts in silico with the target biological component at the given level. According to embodiments of the disclosure, the target assay node and the assay reactant node at the given level and the assay reaction product node at the child level constitute an assay reaction group of one or more assay reaction groups corresponding to the child level.

Figure 12:
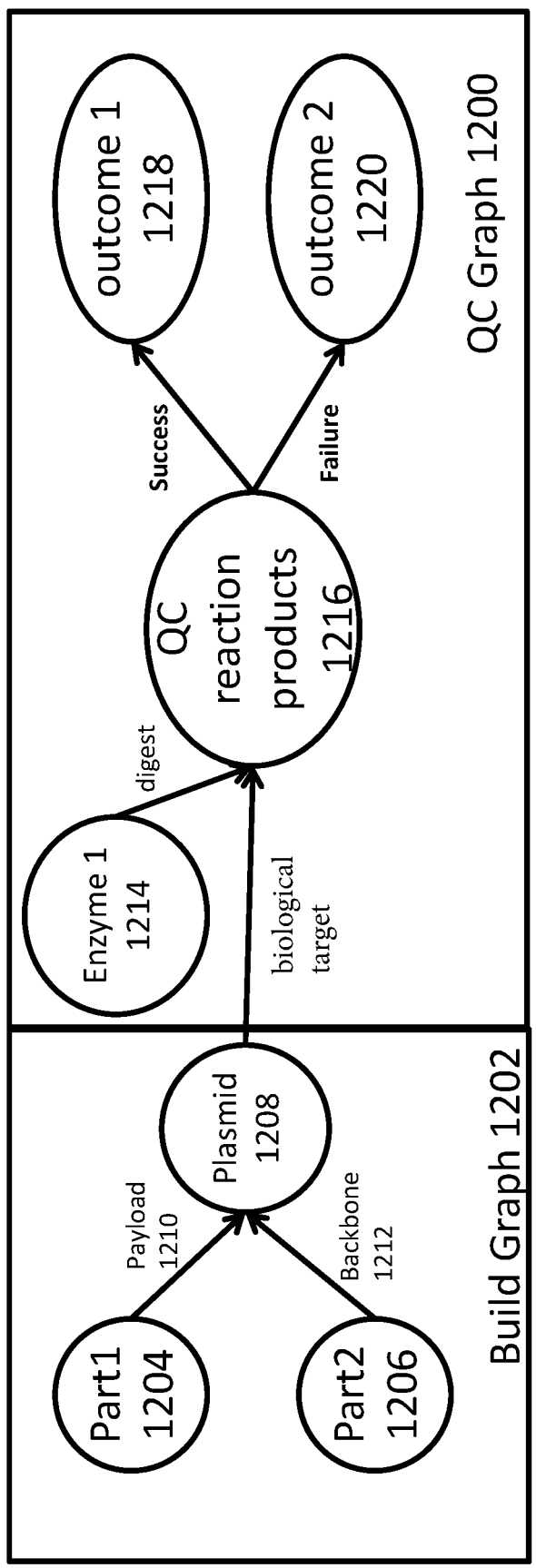
FIG. 12 illustrates a directed graph representing quality control testing, according to embodiments of the present disclosure.

As an example, FIG. 12 illustrates a QC graph data structure 1200 for designing QC testing on the product of a reaction group. The reaction group is illustrated as a build graph data structure 1202. The reaction group models the reaction of part 1 (node 1204) and part 2 (node 1206). The roles of those parts are stored as edges respectively labeled with the roles payload 1210 and plasmid backbone 1212. The result of the reaction group is a node representing a plasmid 1208.

The QC graph 1200 represents an in silico assay performed on a target biological component, the plasmid (node 1208). For the sake of this example, the node 1208 represents only one target biological component. The graph represents the assay as the reaction of an assay reactant, an enzyme (node 1214), with the plasmid (node 1208) to produce an assay reaction product(s) (node 1216). The node 1216 may represent one or more assay reaction products. The plasmid (node 1208), enzyme (node 1214), and assay reaction product(s) (node 1216) together constitute an assay reaction group.

According to embodiments of the disclosure, during QC test design, the QC test design engine compares attributes of the assay reaction products to reference information (e.g., expected number of reaction products, expected length thereof, expected sequence thereof) in order to classify the target biological component as belonging to one or more success or failure modes. The QC test design engine may store the associations of the success and failure modes with the corresponding subset of reaction products for the target biological component as nodes 1218 and 1220, respectively.

According to embodiments of the disclosure, the QC test design engine or another computing device may store reference information from assays that result in successful and failed outcomes. For example, reference information from an assay on a biological component similar to, but not the same as the target biological component would correspond to a failure mode. As another example, reference information from an assay on the target biological component using an enzyme reactant with a known defect would correspond to another failure mode.

Embodiments of the disclosure mitigate challenges of designing QC tests for high throughput strain design systems by taking common aspects of similar QC tests out of their specific context and performing them together. Embodiments of the disclosure allow common processing of steps for many different QC assays where the assays share the same assay reaction steps, similar to the manner in which other embodiments of the disclosure discern common parts of disparate biological processes and group them together on a factory order scale. According to embodiments of the disclosure, each assay comprises one or more assay phases, and each assay phase comprises an assay reaction step of a plurality of assay reaction steps.

According to embodiments of the disclosure, the QC test design engine determines that one or more assay phases of different assays are common assay phases that may be processed together based at least in part upon a commonality of the one or more assay reaction steps of the common assay phases, and generates the assay data structure based at least in part upon the common assay phases. The common assay phases may be associated with the same assay reactant.

According to embodiments of the disclosure, the QC test design engine determines the quantity of assay reactant needed for the common assay phases. For example, if two common assay phases perform the same assay reaction step on two different biological components, the QC test design engine can compute the total amount of assay reactants needed for the common assay phases, and assign performance of the common assay phases to the appropriate physical laboratory equipment in an efficient manner. According to embodiments of the disclosure, during performance of the quality control testing in the physical world, the test equipment 212 traverses the QC test data structure (e.g., a directed graph of the data structure) to determine the amount of reactant to be used at each piece of physical laboratory equipment for the QC assays.

According to embodiments of the disclosure, the test equipment 212 traverses the QC test data structure to identify all target biological components with a shared reactant (e.g., enzyme) and instructs the laboratory equipment (e.g., robots) to place each of those target biological components in the same plate, thereby minimizing the complexity of distributing the enzyme to those samples. For example, assume QC testing of 400 plasmids. If an assay requires 80 of the 400 plasmids to be digested by enzyme 1, and those 80 different plasmids are mixed with the other 320 plasmids on five different plates, then the robot chosen to dispense enzyme 1 has to have all 5 plates sent to it. Thus, it would take a long time to transfer the enzyme and would complicated to organize. However, according to embodiments of the disclosure, the test equipment instructs placement on the same plate of the 80 plasmids to be digested with enzyme. Thus, only one plate has to be sent to the robot, all the transfers can be done at once, it is faster and much less complicated.

Figure 13:
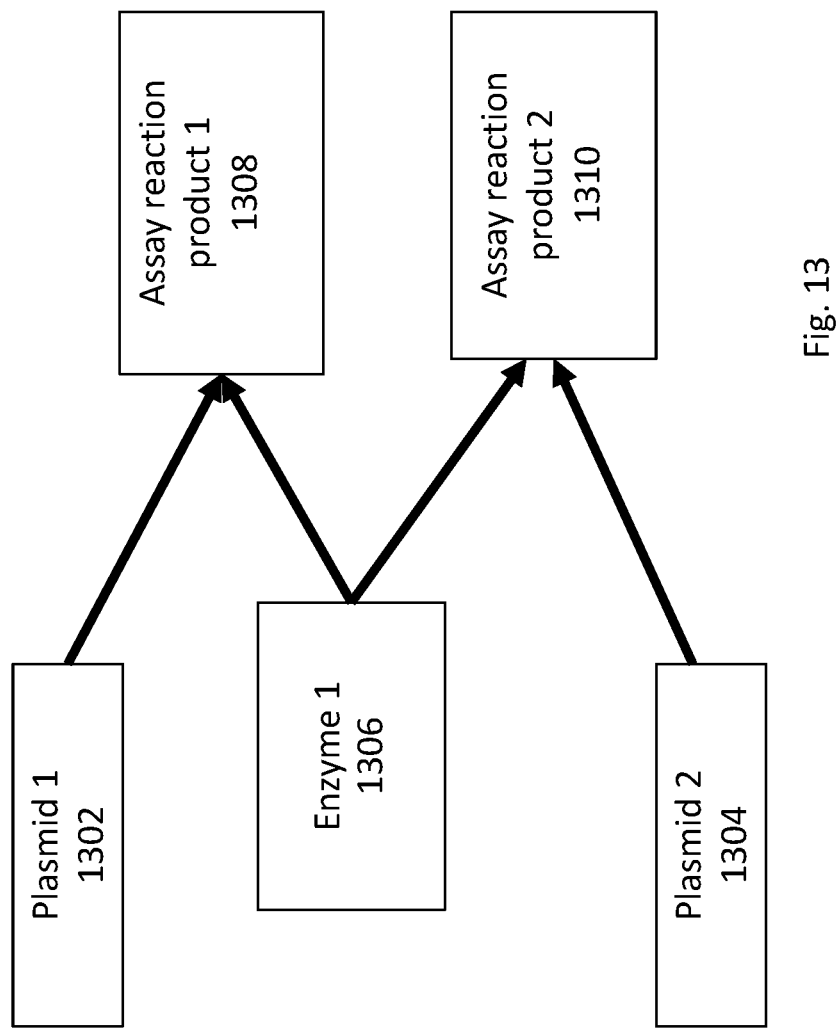
FIG. 13 is an example QC graph illustrating how embodiments of the disclosure enable design of QC tests that efficiently use the same assay reactant in different assay reactions.

FIG. 13 is an example QC graph illustrating how embodiments of the disclosure enable design of QC tests that efficiently use the same assay reactant in different assay reactions. Nodes 1302, 1304 respectively represent target biological components plasmid 1 and plasmid 2. Each assay reaction on each plasmid requires a reaction with an enzyme, Enzyme 1. The reactions with plasmid 1 and plasmid 2 result in assay reaction product 1 (node 1308) and assay reaction product 2 (node 1310), respectively. According to embodiments of the disclosure, the QC test design engine recognizes the common use of Enzyme 1 in both assay reactions and constructs the data structure to reflect that common use, as shown in the figure, by representing Enzyme 1 with only a single assay node shared by two different assay reaction groups. Similar to the embodiments described with respect to FIG. 8, the data structure (e.g., the nodes) stores properties of the represented biological components and reactions (e.g., as annotations). The QC test design engine may use this information to calculate volume, concentration or other quantities of, e.g., Enzyme 1, required to perform the assays.

According to embodiments of the disclosure, classifying comprises classifying the expected outcome of each assay as at least two failure modes based at least in part upon empirical information concerning the assay. According to embodiments of the disclosure, a failure mode represents a defect of the target biological component. According to embodiments of the disclosure, a failure mode represents a failure of the assay. According to embodiments of the disclosure, a first failure mode represents an improperly constructed target biological component according to a first construction error (e.g., too many or two few parts compared to expected number), and a second failure mode represents an improperly constructed target biological component according to a second construction error (e.g., part inserted in reverse order). According to embodiments of the disclosure, a failure mode represents a defective assay reactant. Embodiments of the disclosure may classify the expected assay outcomes according to any combination of the above success and failure modes.

According to embodiments of the disclosure, for the one or more assay reaction products of an assay reaction, the reference information further comprises identification of: the assay reaction, the one or more assay reaction products, or the assay reactant. The reference information atttributes may include expected length, sequence, or growth capacity of the one or more assay reaction products.

According to embodiments of the disclosure, each of the one or more target biological components is produced in accordance with at least a portion of a build graph data structure, where each node that resides at a level of a plurality of levels of the build graph data structure represents at least one of one or more biological components. According to embodiments of the disclosure, the build graph data structure controls production in a gene manufacturing system of a product of interest, wherein the product of interest incorporates genetic modifications represented by the build graph.

According to embodiments of the disclosure, one or more source nodes, at a given level of the plurality of levels of the build graph data structure, and a destination node, at a child level of the given level of the build graph data structure, that is associated with the one or more source nodes, constitute a reaction group of one or more reaction groups corresponding to the child level of the build graph data structure. According to embodiments of the disclosure, each reaction group represents a reaction between one or more biological components that are themselves represented by the one or more source nodes at the given level, to produce one or more of the target biological components represented by the destination node of the reaction group at the child level of the build graph data structure.

QC Test Implementation

According to embodiments of the disclosure, the biological components assembled at the factory 210 are tested using test equipment 212. During testing, the biological components are subjected to quality control assessments based upon size and sequencing, among other methods. According to embodiments of the disclosure, QC is performed on intermediate biological components and not just the final product of interest produced by the factory 210. The resulting, modified biological components that pass QC may then be transferred from liquid or colony cultures on to plates, or otherwise further processed in furtherance of manufacturing the final product of interest. According to embodiments of the disclosure, the test equipment 212 performs quality control testing on a target biological component (e.g., an intermediate or final product), by obtaining information concerning one or more physical assay reaction products resulting from a physical assay of a target biological component; and comparing the one or more physical assay reaction products to corresponding reference information to classify the target biological component as corresponding to at least one success mode, to at least one failure mode, or to an indeterminate mode wherein the reference information includes expected attributes of the one or more physical assay reaction products corresponding to success and failure modes. The library 206 or another database may store the reference information.

If the target biological component is classified as corresponding to the indeterminate mode, the test equipment 212 of embodiments of the disclosure indicates that the physical assay should be performed again. If the target biological component is classified as corresponding to the at least one success mode, the test equipment 212 of embodiments of the disclosure provides instructions for further processing of the target biological component in furtherance of producing a product of interest. A failure mode may represent a defect of the target biological component. A failure mode may represent a failure of the physical assay. According to embodiments of the disclosure, a first failure mode represents an improperly constructed target biological component according to a first construction error, and a second failure mode represents an improperly constructed target biological component according to a second construction error. According to embodiments of the disclosure, a failure mode represents a defective assay reactant used in a physical assay reaction of the physical assay. The test equipment 212 of embodiments of the disclosure may classify the target biological component according to any combination of the above success, failure and indeterminate modes.

Referring to FIG. 12, according to embodiments of the disclosure the test equipment 212 instructs physical laboratory equipment to perform an in vitro assay of the physical plasmid (corresponding to node 1208), which has been produced by factory 210. The test equipment 212 causes the enzyme (node 1214) to be reacted with the plasmid, in order to form physical reaction products (corresponding to node 1216). The test equipment 1212 compares the physical reaction products with the reference information to classify the plasmid as corresponding to one or more success or failure modes, or as neither (e.g., indeterminate).

Computer System

FIG. 7 shows an example of a computer system 800 that may be used to execute program code stored in a non-transitory computer readable medium (e.g., memory) in accordance with embodiments of the disclosure. The computer system includes an input/output subsystem 802, which may be used to implement input interface 202 to interface with human users and/or other computer systems depending upon the application. For example, the editor of embodiments of the disclosure may be implemented in program code on system 800 with I/O subsystem 802 used to receive input program statements from a human user (e.g., via a GUI or keyboard) and to display them back to the user. The I/O subsystem 802 may include, e.g., a keyboard, mouse, graphical user interface, touchscreen, or other interfaces for input, and, e.g., an LED or other flat screen display, or other interfaces for output. Other elements of embodiments of the disclosure, such as the workflow engine 1002, or the order placement engine 208, may be implemented with a computer system like that of computer system 800, perhaps, however, with or without I/O.

Program code may be stored in non-transitory media such as persistent storage 810 or memory 808 or both. A processor 804 reads program code from one or more non-transitory media and executes the code to enable the computer system to accomplish the methods performed by the embodiments herein, such as those represented by the flow chart of FIG. 2. Those skilled in the art will understand that the processor may ingest source code, such as statements expressed in the high-level genomic design language of embodiments of the disclosure, and interpret or compile the source code into machine code that is understandable at the hardware gate level of the processor. A bus couples the I/O subsystem 802, the processor 804, peripheral devices 806, memory 808, and persistent storage 810.

Those skilled in the art will understand that some or all of the elements of embodiments of the disclosure, such as those shown in FIG. 1 (e.g., interpreter, execution engine, order placement engine, factory, test equipment, analysis equipment), (and their accompanying operations, such as those shown in FIG. 2), or such as those shown in FIG. 10 (e.g., workflow engine), may be implemented wholly or partially on one or more computer systems including one or more processors and one or more memory systems like those of computer system 800. Some elements and functionality may be implemented locally and others may be implemented in a distributed fashion over a network through different servers, e.g., in client-server fashion, for example.

Figure 11:
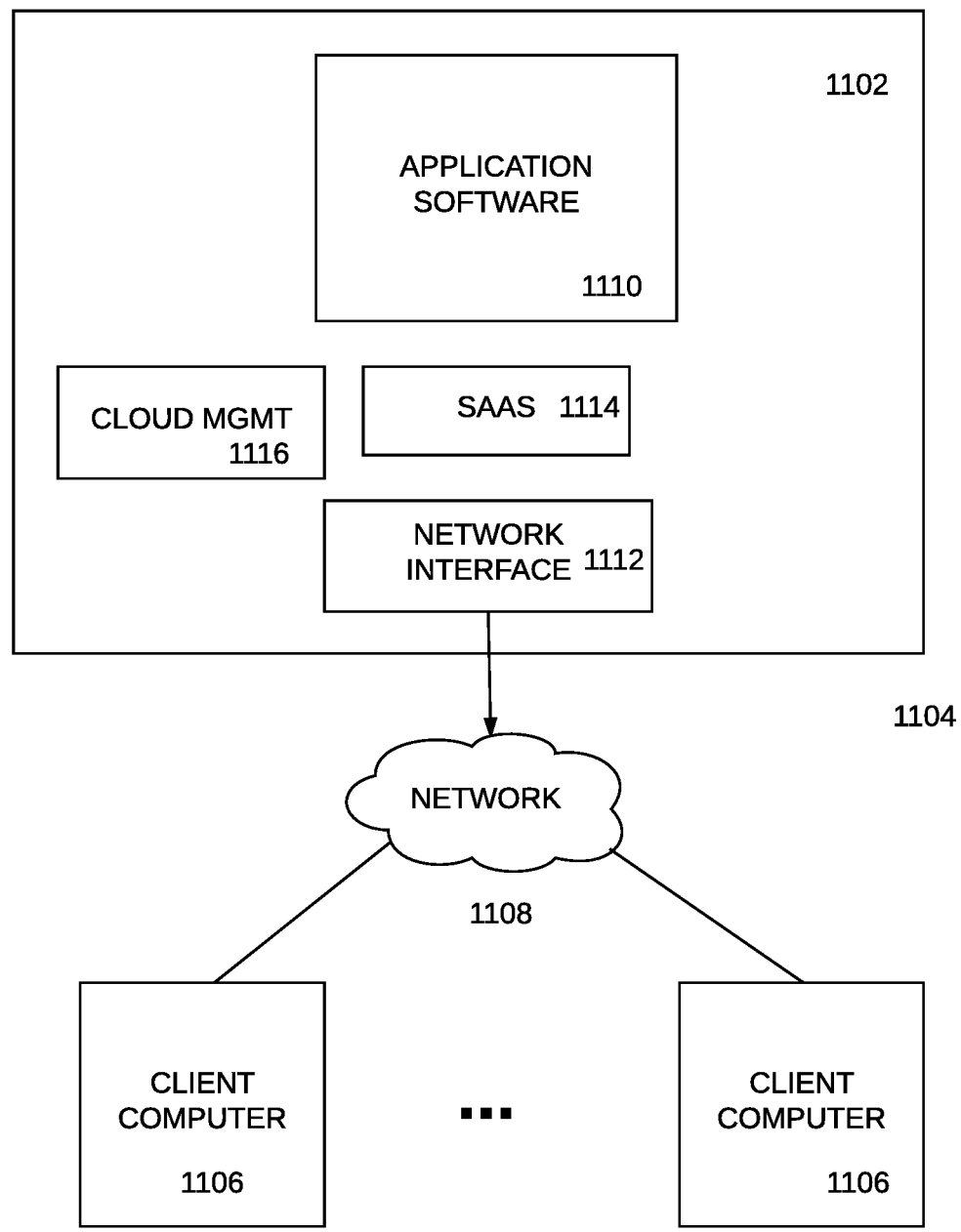
FIG. 11 illustrates a cloud computing environment according to embodiments of the present disclosure.

FIG. 11 illustrates a cloud computing environment according to embodiments of the present disclosure. In embodiments of the disclosure, the LIMS or the FESI application software 1110 may be implemented in a cloud computing system 1102, to enable multiple users to access those systems according to embodiments of the present disclosure. Client computers 1106, such as those illustrated in FIG. 7, access the system via a network 1108, such as the Internet. The system may employ one or more computing systems using one or more processors, of the type illustrated in FIG. 7. The cloud computing system itself includes a network interface 1112 to interface the software 1110 to the client computers 1106 via the network 1108. The network interface 1112 may include an application programming interface (API) to enable client applications at the client computers 1106 to access the system software 1110.

A software as a service (SaaS) software module 1114 offers the system software 1110 as a service to the client computers 1106. A cloud management module 1116 manages access to the software 1110 by the client computers 1106. The cloud management module 1116 enables a cloud architecture that may employ multitenant applications, virtualization or other architectures known in the art to serve multiple users.

While embodiments of the disclosure have been particularly described with respect to the illustrated embodiments, it will be appreciated that various alterations, modifications and adaptations may be made based on the present disclosure, and are intended to be within the scope of the present invention. While embodiments of the disclosure have been described in connection with the disclosed embodiments, it is to be understood that the present invention is not limited to the disclosed embodiments but, on the contrary, is intended to cover various modifications and equivalent arrangements included within the scope of the claims.

APPENDIX 1

Function Reference

This appendix describes some of the available functions in the built-in library for the Codon language in the LIMS.
circularize
circularize(input: DnaInput) -> DnaSpec
circularize(input: DnaInput, originShift: Int) -> DnaSpec
Returns a DnaSpec representing the circularized forms of the DNA input(s). If originShift is specified, this shifts the origin downstream (with wraparound) by originShift base pairs.
concat
concat[x](left: DnaInput, right: DnaInput) -> DnaSpec
Concatenates the left and right arguments. Function-call synonym for left * right or left x right depending on the operator modifier chosen.
dna
dna(dnaSeq: String) -> DnaComp
dna(dnaSeq: String, name: String) -> DnaComp
Returns a DnaComponent encapsulating the DNA sequence represented by the specified string. You may optionally specify a name for the created DnaComponent.
ecoRV = dna("GATATC") # Define an enzyme binding site
ecoRV2 = dna("GATATC", "ecoRV") # ... Create a named DnaComponent.
dnaComponent
dnaComponent(zid: Int) -> DnaComp
dnaComponent(name: String) -> DnaComp
Connect to LIMS library and load the DnaComponent with the specified ZId or name.
myDnaComponent = dnaComponent(13000000001)
dnaForStrain
dnaForStrain(zid: Int) -> DnaComp
dnaForStrain(name: String) -> DnaComp
Load the DnaComp associated with the strain with the specified ZId or name.
* * * * * * * * * * *
baseStrainDna = dnaForStrain(7000000001)
dnaSpecification
dnaSpecification(zid: Int) -> DnaSpec
dnaSpecification(name: String) -> DnaSpec
Connect to LIMS and load the DnaSpecification with the specified ZId or name.
myDnaSpec = dnaSpecification(18000000001)
hello
hello(name: String) -> String
Returns a friendly greeting to the specified name. As you might imagine, this is mostly useful for playing around.
print hello("Bob") # prints "Hello, Bob" to the screen.
len
len(list: List[Any]) -> Int
len(map: Map[Any]) -> Int
len(str: String) -> Int
Return the length of the specified list, map or string.

APPENDIX 1-continued

Function Reference listSpec
listSpec(lst: List[DnaComp]) -> DnaSpec
listSpec(lst: List[DnaSpec]) -> DnaSpec
Take a list of DnaComps or DnaSpecs and create a DnaSpec that enumerates these inputs. See also: partsList( )
partsList
partsList(parts: List[DnaInput], groupName: String) -> DnaSpec
partsList(parts: List[DnaInput], groupName: String, leftLen: Int, rightLen: Int) -> DnaSpec
Creates a DnaSpec representing a parts list with the specified properties. The output DnaSpec will have the groupName property set according to the argument. If left and right tail lengths are not provided, then they will be set to zero in the DnaSpec. Otherwise, the specified left and right tail lengths will be used. The parameters for groupName, leftTailLen and rightTailLen specified by any prior setparam statements will be ignored.
Using this function is equivalent to the following:
myParts = [ ... ] # Set to a list of DnaSpecs, DnaComps, etc.
setparam "amplifyPart", "true"
setparam "groupName", myGroupName
setparam "leftTailLen", myLeftLen
setparam "rightTailLen", myRightLen
myPartsList = listSpec(myParts)
clearparams # or otherwise revert amplifyPart/groupName/leftTailLen/rightTailLen.
See also: listSpec( ).
toSeq
toSeq(dna: DnaComponent) -> String
Return the DNA sequence underlying a DnaComponent as a string.
toString
toString(val: Any) -> String
toString(val: Any, recursive: Int) -> String
Converts the specified value to a string. The recursive argument is a boolean flag (use constants true or false) to indicate whether DnaSpec structures should be recursively looked up.
print toString(foo) # Print the value of 'foo' to the output.
print toString(myDnaSpec, true) # Print an entire DnaSpecification and its children
proswp
proswp[x](baseStrain: LocatedDnaSpec, promoters: DnaInput) -> DnaSpec
proswp[x](baseStrain: LocatedDnaSpec, promoters: DnaInput, allowInsert: Int) -> DnaSpec
Performs the promoter swap associated with inserting the specified promoter(s) immediately upstream of the genes identified in located baseStrain, replacing the previous driving promoter.
If 'allowInsert' is specified, this should be 'true' to allow insertion of promoters if no existing promoter is driving the specified gene, or 'false' to fail if no driving promoter exists to replace.
replace
replace[x](baseStrain: LocatedDnaSpec, insertions: DnaInput) ->
At the specified location(s) of the base strain(s), replace the subsequence identified in the location with the new sequences specified by 'insertions'.
You may specify multiple insertions in 'insertions'. Depending on whether the cross ('[x]') or dot ('[*]') operator is chosen, this will place one insertion in each yielded location in 'baseStrain', or apply each insertion to each possible location.
The replacement operation may specify a strict insertion operation that replaces an empty replaceable region with the replacement sequence part "insertions". Alternatively, the replacement operation may specify a strict deletion operation that replaces the replaceable region with an empty replacement sequence part.
locate, locateName, locateTerm
locate(baseStrain: DnaInput, offset: Int) -> LocatedDnaSpec
locate[x](baseStrain: DnaInput, offset: List[Int]) -> LocatedDnaSpec
locate(baseStrain: DnaInput, offset: Int, length: String) -> LocatedDnaSpec
locate[x](baseStrain: DnaInput, offset: List[Int], length: List[String]) -> LocatedDnaSpec
locate(baseStrain: DnaInput, offset: Int, subseq: String) -> LocatedDnaSpec
locate[x](baseStrain: DnaInput, offset: List[Int], subseq: List[String]) -> LocatedDnaSpec
locateName(baseStrain: DnaInput, annotationName: String) -> LocatedDnaSpec
locateName[x](baseStrain: DnaInput, annotationNames: List[String]) -> LocatedDnaSpec
locateTerm(baseStrain: DnaInput, annotationTerm: String) -> LocatedDnaSpec
locateTerm[x](baseStrain: DnaInput, annotationTerms: List[String]) -> LocatedDnaSpec
Given some DnaInput, return a LocatedDnaSpec that wraps around it. The LocatedDnaSpec contains the same outputs, but with location information about the identified region returned in an output parameter. TheLocatedDnaSpec is a DnaSpecification whose function is LOCATE. The region identification is made via the parameters map within the DnaSpecification.
The location can be either a single base, or a region extending over many bases.
The location is specified as either a single offset, or a region extending from 'offset' to 'offset + length', or 'offset + len(subseq)'. In the latter case, 'subseq' must be the exact-matching DNA sequence starting at 'offset'.
A location can also be given as the (unique) name of an annotated region in each base strain element. The located region is the entire extent of the annotation.

APPENDIX 1-continued

Function Reference

If multiple annotations or offset/offset+length/offset+subseq values are given,
then these are applied one-at-a-time to individual elements of 'baseStrain', or
all applied to all elements of 'baseStrain' depending on whether the dot ('[*]')
or cross ('[x]') operator is chosen, respectively.
Annotation-based locations can be specified as either a specific annotation name
to return (in which case they should return a single location per input genome)
or the annotation's sequence feature term name (in which case, many locations per
input genome may be returned).
A LocatedDnaSpec can be used as the input to functions such as 'insert', 'replace',
and 'delete'. When removing bases from the DNA sequence (e.g., as in 'replace'
and 'delete'), the amount to remove is specified as a parameter to 'locate( )',
either in a number of base pairs, or in the specific subsequence to remove. That
is, the entire located region is removed by 'replace' or 'delete'.
You may specify an empty subsequence or a length of 0 to indicate no deletion
(e.g., the 'replace' function is being used for pure insertion).
Offsets begin at 1 and run up to and including '|the DNA sequence|'. Consider
the following example:
'''
input = dna("AATTCG")
replace[x](locate(input, 3, 1), dna("A")) // Returns "AAATCG"
'''
insert
insert[x](baseStrain: LocatedDnaSpec, insertions: DnaInput) -> DnaSpec
At the specified locations of the base strain, insert the specified insertions.
If the 'baseStrain' or 'insertions' are multiple inputs, then the insertions
are performed in a dot or a cross product with the elements of 'baseStrain'
per the function call modifier.
insertDownstream
insertDownstream[x](baseStrain: LocatedDnaSpec, insertions: DnaInput) -> DnaSpec
Inserts the DNA specified by 'insertions' immediately after the specified
annotation in the base strain, relative to the direction of the annotation. That
is, in a "forward" annotation, inserts to the right of the annotated sequence
(as read from 5' to 3'); in a reverse annotation, inserts to the left.
If the 'baseStrain' or 'insertions' DnaInputs represent multiple inputs, the
insertions are made as a dot or cross product of all 'baseStrain' instances with all
'insertion' instances per the function call modifier.
insertUpstream
insertUpstream[x](baseStrain: LocatedDnaSpec, insertions: DnaInput) -> DnaSpec
Inserts the DNA specified by 'insertions' immediately before the specified
annotation in the base strain, relative to the direction of the annotation. That
is, in a "forward" annotation, inserts to the left of the annotated sequence
(as read from 5' to 3'); in a reverse annotation, inserts to the right.
If the 'baseStrain' or 'insertions' DnaInputs represent multiple inputs, the
insertions are made as a dot or cross product of all 'baseStrain' instances with all 'insertion'
instances per the function call modifier.

---

What is claimed is:

1. One or more non-transitory computer-readable media storing instructions for generating a build graph data structure to control production in a gene manufacturing system of at least one product of interest incorporating genetic modifications, wherein the instructions, when executed by one or more computing devices, cause at least one of the one or more computing devices to:
   access a description of a biological workflow, wherein the description includes representations of biological components; and
   assemble a build graph data structure based at least in part upon the workflow description,
   wherein, in the build graph data structure, each biological component is represented by a node that resides at a level of a plurality of levels,
   wherein one or more source nodes, at a given level of the plurality of levels, and a destination node, at a child level of the given level, constitute a reaction group of one or more reaction groups corresponding to the child level,
   wherein each reaction group represents a reaction between one or more biological components that are themselves represented by the one or more source nodes at the given level, to produce a biological component represented by the destination node of the reaction group at the child level,
   wherein one or more destination nodes at the child level act as one or more source nodes in a reaction group of one or more reaction groups at a grandchild level of the given level, and
   wherein at least one destination node at a final level of the plurality of levels represents the at least one product of interest, which incorporates genetic modifications caused by reactions among biological components at different levels, and
   wherein processing the build graph data structure results in production of the at least one product of interest.

2. The one or more non-transitory computer-readable media of claim 1, wherein the at least one product of interest comprises a nucleotide sequence or a microbial strain.

3. The one or more non-transitory computer-readable media of claim 1, wherein at least one of the one or more source nodes at the given level belongs to two different reaction groups.

4. The one or more non-transitory computer-readable media of claim 1, storing further instructions for:
   determining that two or more workflow phases for different factory orders are common workflow phases that may be processed together based at least in part upon a commonality of reaction steps of the common workflow phases,
   wherein assembling the build graph data structure is based at least in part upon the common workflow phases.

5. The one or more non-transitory computer-readable media of claim 1, wherein a first destination node in a first reaction group of the one or more reaction groups represents a non-deterministic set of biological components computed to result from one or more reactions applied to one or more biological components represented by the one or more source nodes in the first reaction group.

6. The one or more non-transitory computer-readable media of claim 1, wherein each first biological component is a nucleotide and the second biological component is a nucleotide sequence.

7. The one or more non-transitory computer-readable media of claim 1, wherein a first source node at the given level within a reaction group represents a plurality of first biological components, or the destination node at the child level represents a plurality of second biological components.

8. One or more non-transitory computer-readable media storing instructions for processing factory orders to control production in a gene manufacturing system of one or more products of interest incorporating genetic modifications, wherein the instructions, when executed by one or more computing devices, cause at least one of the one or more computing devices to:
   access a plurality of factory orders, wherein each factory order indicates one or more genetic design techniques for building one or more products of interest;
   determine that two or more workflow phases for workflows for constructing different factory orders of the plurality of factory orders are common workflow phases that may be processed together based at least in part upon a commonality of reaction steps of the common workflow phases, wherein each workflow comprises a series of workflow phases, and each workflow phase comprises one or more reaction steps; and
   generate a build graph data structure based at least in part upon the common workflow phases, wherein processing the build graph data structure results in production of the one or more products of interest.

9. The one or more non-transitory computer-readable media of claim 8, wherein a destination node, at a given level of the build graph data structure, that represents the processing of the common workflow phases, serves as a source node, at the given level, that connects to two or more destination nodes at a child level of the given level.

10. The one or more non-transitory computer-readable media of claim 8, storing further instructions for determining the two or more common workflow phases based at least in part upon the different factory orders.

11. One or more non-transitory computer-readable media storing instructions for processing a build graph data structure to control production in a gene manufacturing system of a product of interest that incorporates genetic modifications, wherein the instructions, when executed by one or more computing devices, cause at least one of the one or more computing devices to:
   access a build graph data structure comprising a plurality of nodes, wherein
      each node represents a biological component and resides at a level of a plurality of levels,
      one or more source nodes, at given level of the plurality of levels, and a destination node, at a child level of the given level, constitute a reaction group of one or more reaction groups corresponding to the child level, and
      each reaction group represents a reaction between the one or more biological components that are themselves represented by the one or more source nodes at the given level to produce a biological component represented by the destination node of the reaction group at the child level; and
   traverse the build graph data structure at the plurality of levels to map the biological components corresponding to the nodes at the plurality of levels to physical laboratory equipment, wherein operation of the physical laboratory equipment leads to production of the product of interest.

12. The one or more non-transitory computer-readable media of claim 11, storing further instructions for determining the number of source physical media for sourcing transfer of a corresponding biological component to produce the biological component represented by the destination node within each reaction group at the child level based at least in part upon the amount of biological component within the source physical media.

13. The one or more non-transitory computer-readable media of claim 11, wherein traversing the build graph data structure comprises determining one or more layouts of biological components on physical media of one or more respective physical carriers.

14. The one or more non-transitory computer-readable media of claim 11, wherein determining one or more layouts of biological components on physical media is based at least in part upon optimizing one or more layouts for efficient transfer of biological components from source physical media to destination physical media.

15. The one or more non-transitory computer-readable media of claim 11, storing further instructions for:
   receiving a final layout of biological components on physical media of a final physical carrier,
      wherein each biological component of the final layout is represented by a destination node at a final level of the build graph data structure,
      wherein traversing further comprises determining one or more layouts of biological components on physical media of one or more respective physical carriers at corresponding one or more non-final levels of the plurality of levels.

16. The one or more non-transitory computer-readable media of claim 11, wherein the product of interest comprises a nucleotide sequence or a microbial strain.

17. One or more non-transitory computer-readable media storing instructions for implementation of biological protocols on a plurality of automated equipment to generate a product of interest that incorporates genetic modifications, wherein different ones of the automated equipment implement biological protocols pursuant to machine-specific instructions in respective, different machine-specific languages, wherein the instructions, when executed by one or more computing devices, cause at least one of the one or more computing devices to:
   issue object instructions based at least in part upon one or more factory orders, the object instructions for instructing the plurality of automated equipment to execute biological protocols; and
   translate object instructions into machine-specific instructions in a machine-specific language of a plurality of machine-specific languages,
   wherein each automated equipment is operable to execute machine-specific instructions in a respective machine-specific language to implement a biological protocol to generate a biological component along a path to generating the product of interest, and at least two automated equipment operate pursuant to different machine-specific languages.

18. The one or more non-transitory computer-readable media of claim 17 storing further instructions for generating a build graph data structure representing common workflow phases for different factory orders.

19. The one or more non-transitory computer-readable media of claim 17, storing further instructions for:
  determining one or more automated equipment that are available to run the biological protocol based at least in part upon messages related to the one or more automated equipment,
  directing object instructions to the available automated equipment.

20. The one or more non-transitory computer-readable media of claim 17, wherein the protocol comprises transferring biological components from source physical carriers to destination physical carriers.

21. One or more non-transitory computer-readable media storing instructions for designing quality testing of a plurality of biological components, wherein the instructions, when executed by one or more computing devices, cause at least one of the one or more computing devices to:
  perform, in silico, one or more assays on one or more target biological components, the in silico performance of each assay on one of the one or more biological components producing one or more assay reaction products resulting from an assay reaction involving the one of the one or more target biological components;
  classify two or more expected outcomes of each assay as being from the group of: at least one success mode or at least one failure mode, based at least in part upon empirical information concerning the assay; and
  store, in an assay data structure, for the one or more assay reaction products, reference information including: (a) attributes of the one or more assay reaction products, and (b) the classification of the two or more expected outcomes,
  wherein processing of the assay data structure results in: (a) performing one or more physical assays, corresponding to the one or more in silico assays, on the one or more target biological components using physical laboratory equipment to generate one or more physical assay reaction products for each physical assay, and (b) for each physical assay, comparing the one or more physical assay reaction products to corresponding reference information to classify the target biological component as corresponding to the at least one success mode or the at least one failure mode.

22. The one or more non-transitory computer-readable media of claim 21, wherein the assay data structure is a directed graph that includes, for the one or more assays on the one or more target biological components, a plurality of levels including a plurality of assay nodes, wherein, in the directed graph:
  each assay node that resides at a level of a plurality of levels represents one of the one or more of the target biological components, one or more assay reactants, or one or more of the assay reaction products,
  a target assay node of the plurality of assay nodes represents, at a given level, a target biological component of the one or more target biological components,
  an assay reaction product node, of the plurality of assay nodes, that is associated with the target assay node, and represents, at a child level of the given level, the one or more assay reaction products and the reference information.

23. The one or more non-transitory computer-readable media of claim 21, wherein the given level includes at least one assay reactant node representing at least one assay reactant that reacts in silico with the target biological component at the given level.

24. The one or more non-transitory computer-readable media of claim 21, wherein the target assay node and the assay reactant node at the given level and the assay reaction product node at the child level constitute an assay reaction group of one or more assay reaction groups corresponding to the child level.

25. The one or more non-transitory computer-readable media of claim 21, wherein each assay comprises one or more assay phases, and each assay phase comprises an assay reaction step of a plurality of assay reaction steps, the one or more non-transitory computer-readable media storing instructions, that when executed, cause at least one of the one or more computing devices to:
  determine that one or more assay phases of different assays are common assay phases that may be processed together based at least in part upon a commonality of the one or more assay reaction steps of the common assay phases; and
  generate the assay data structure based at least in part upon the common assay phases.

26. The one or more non-transitory computer-readable media of claim 21, wherein performing, in silico, one or more assays on one or more target biological components comprises performing, in silico, at least two assays of the one or more assays on a first target biological component of the one or more target biological components.

27. The one or more non-transitory computer-readable media of claim 21, wherein the one or more target biological components comprise a plasmid, and the one or more reaction products comprise plasmid fragments.

28. The one or more non-transitory computer-readable media of claim 21, wherein each of the one or more target biological components comprises a nucleotide sequence or a microbial strain.

29. The one or more non-transitory computer-readable media of claim 21, wherein
  each of the one or more target biological components is produced in accordance with at least a portion of a build graph data structure,
  each node that resides at a level of a plurality of levels of the build graph data structure represents at least one of one or more biological components, the build graph data structure for controlling production in a gene manufacturing system of a product of interest, wherein the product of interest incorporates genetic modifications represented by the build graph,
  wherein one or more source nodes, at a given level of the plurality of levels of the build graph data structure, and a destination node, at a child level of the given level of the build graph data structure, that is associated with the one or more source nodes, constitute a reaction group of one or more reaction groups corresponding to the child level of the build graph data structure,
  wherein each reaction group represents a reaction between one or more biological components that are themselves represented by the one or more source nodes at the given level, to produce one or more of the target biological components represented by the destination node of the reaction group at the child level of the build graph data structure.

30. One or more non-transitory computer-readable media storing instructions for performing quality testing of a target biological component, wherein the instructions, when executed by one or more computing devices, cause at least one of the one or more computing devices to:

obtain information concerning one or more physical assay reaction products resulting from a physical assay of a target biological component; and compare the one or more physical assay reaction products to corresponding reference information to classify the target biological component as corresponding to at least one success mode, to at least one failure mode, or to an indeterminate mode, wherein the reference information includes expected attributes of the one or more physical assay reaction products corresponding to success and failure modes.

31. The one or more non-transitory computer-readable media of claim 30, storing instructions, that when executed, cause at least one of the one or more computing devices to:

if the target biological component is classified as corresponding to the at least one success mode, provide instruction for further processing of the target biological component in furtherance of producing a product of interest.

32. One or more non-transitory computer-readable media storing instructions for generating a factory order to control production of biological sequences by a gene manufacturing system, wherein the instructions, when executed by one or more computing devices, cause at least one of the one or more computing devices to:

receive an expression indicating a non-deterministic operation on a first sequence operand, wherein sequence operands represent biological sequence parts, the first sequence operand representing one or more biological sequence parts;

execute instructions to evaluate the expression to a sequence specification, wherein the sequence specification comprises a data structure including (a) one or more first-level non-deterministic operations, including the first non-deterministic operation, to be performed on one or more first-level sequence operands including the first sequence operand, and (b) one or more second-level operations, the execution of which resolves one or more values of the one or more first-level sequence operands; and generate a factory order based upon execution, by a computing device, of one or more of the first-level operations and one or more of the second-level operations, the factory order for use by the gene manufacturing system to generate biological sequence parts, wherein the one or more first-level non-deterministic operations correspond to protocols for generating the biological sequence parts.

33. The one or more non-transitory computer-readable media of claim 32, wherein the one or more first-level non-deterministic operations also correspond to physical laboratory equipment for generating the biological sequence parts.

34. The one or more non-transitory computer-readable media of claim 32, wherein a directed build graph data structure is used in generating the factory order, and one or more non-transitory computer-readable media store instructions, that when executed, cause the at least one of the one or more computing devices to:

determine that two or more workflow phases for different factory orders are common workflow phases that may be processed together based at least in part upon a commonality of reaction steps of the common workflow phases; and assemble the build graph data structure based at least in part upon the common workflow phases.

\* \* \* \* \*

SEQUENCE LISTING

```
<160> NUMBER OF SEQ ID NOS: 19

<210> SEQ ID NO 1
<211> LENGTH: 10
<212> TYPE: DNA
<213> ORGANISM: Artificial Sequence
<220> FEATURE:
<223> OTHER INFORMATION: Unknown biological significance

<400> SEQUENCE: 1
aaattccagg                                                              10

<210> SEQ ID NO 2
<211> LENGTH: 10
<212> TYPE: DNA
<213> ORGANISM: Artificial Sequence
<220> FEATURE:
<223> OTHER INFORMATION: Unknown biological significance

<400> SEQUENCE: 2
aaattcccgg                                                              10
```

<210> SEQ ID NO 3
<211> LENGTH: 10
<212> TYPE: DNA
<213> ORGANISM: Artificial Sequence
<220> FEATURE:
<223> OTHER INFORMATION: Unknown biological significance

<400> SEQUENCE: 3
aaattccggg                                                            10

<210> SEQ ID NO 4
<211> LENGTH: 10
<212> TYPE: DNA
<213> ORGANISM: Artificial Sequence
<220> FEATURE:
<223> OTHER INFORMATION: Unknown biological significance

<400> SEQUENCE: 4
aaattcctgg                                                            10

<210> SEQ ID NO 5
<211> LENGTH: 10
<212> TYPE: DNA
<213> ORGANISM: Artificial Sequence
<220> FEATURE:
<223> OTHER INFORMATION: Unknown biological significance

<400> SEQUENCE: 5
aagttccagg                                                            10

<210> SEQ ID NO 6
<211> LENGTH: 10
<212> TYPE: DNA
<213> ORGANISM: Artificial Sequence
<220> FEATURE:
<223> OTHER INFORMATION: Unknown biological significance

<400> SEQUENCE: 6
aagttcccgg                                                            10

<210> SEQ ID NO 7
<211> LENGTH: 10
<212> TYPE: DNA
<213> ORGANISM: Artificial Sequence
<220> FEATURE:
<223> OTHER INFORMATION: Unknown biological significance

<400> SEQUENCE: 7
aagttccggg                                                            10

<210> SEQ ID NO 8
<211> LENGTH: 10
<212> TYPE: DNA
<213> ORGANISM: Artificial Sequence
<220> FEATURE:
<223> OTHER INFORMATION: Unknown biological significance

<400> SEQUENCE: 8
aagttcctgg                                                            10

<210> SEQ ID NO 9
<211> LENGTH: 10
<212> TYPE: DNA
<213> ORGANISM: Artificial Sequence
<220> FEATURE:
<223> OTHER INFORMATION: Unknown biological significance -continued

<400> SEQUENCE: 9
aatttccagg                                                              10

<210> SEQ ID NO 10
<211> LENGTH: 10
<212> TYPE: DNA
<213> ORGANISM: Artificial Sequence
<220> FEATURE:
<223> OTHER INFORMATION: Unknown biological significance

<400> SEQUENCE: 10
aatttcccgg                                                              10

<210> SEQ ID NO 11
<211> LENGTH: 10
<212> TYPE: DNA
<213> ORGANISM: Artificial Sequence
<220> FEATURE:
<223> OTHER INFORMATION: Unknown biological significance

<400> SEQUENCE: 11
aatttccggg                                                              10

<210> SEQ ID NO 12
<211> LENGTH: 10
<212> TYPE: DNA
<213> ORGANISM: Artificial Sequence
<220> FEATURE:
<223> OTHER INFORMATION: Unknown biological significance

<400> SEQUENCE: 12
aatttcctgg                                                              10

<210> SEQ ID NO 13
<211> LENGTH: 10
<212> TYPE: DNA
<213> ORGANISM: Artificial Sequence
<220> FEATURE:
<223> OTHER INFORMATION: Unknown biological significance

<400> SEQUENCE: 13
aacttccagg                                                              10

<210> SEQ ID NO 14
<211> LENGTH: 10
<212> TYPE: DNA
<213> ORGANISM: Artificial Sequence
<220> FEATURE:
<223> OTHER INFORMATION: Unknown biological significance

<400> SEQUENCE: 14
aacttcccgg                                                              10

<210> SEQ ID NO 15
<211> LENGTH: 10
<212> TYPE: DNA
<213> ORGANISM: Artificial Sequence
<220> FEATURE:
<223> OTHER INFORMATION: Unknown biological significance

<400> SEQUENCE: 15
aacttccggg                                                              10

<210> SEQ ID NO 16

```
<211> LENGTH: 10
<212> TYPE: DNA
<213> ORGANISM: Artificial Sequence
<220> FEATURE:
<223> OTHER INFORMATION: Unknown biological significance

<400> SEQUENCE: 16
aacttcctgg                                                          10

<210> SEQ ID NO 17
<211> LENGTH: 19
<212> TYPE: DNA
<213> ORGANISM: Artificial Sequence
<220> FEATURE:
<223> OTHER INFORMATION: Unknown biological significance

<400> SEQUENCE: 17
tcgacgtgac tagctacgt                                                19

<210> SEQ ID NO 18
<211> LENGTH: 31
<212> TYPE: DNA
<213> ORGANISM: Artificial Sequence
<220> FEATURE:
<223> OTHER INFORMATION: Unknown biological significance

<400> SEQUENCE: 18
gtcagacgta gactgactga tcgacgatca g                                  31

<210> SEQ ID NO 19
<211> LENGTH: 10
<212> TYPE: DNA
<213> ORGANISM: Artificial Sequence
<220> FEATURE:
<223> OTHER INFORMATION: Unknown biological significance

<400> SEQUENCE: 19
agctgagtca                                                          10
```